(12) United States Patent  
Zarbatany et al.

(10) Patent No.: US 12,290,694 B2  
(45) Date of Patent: May 6, 2025

(54) ATRIAL APPENDAGE OCCLUSION AND ARRHYTHMIA TREATMENT

(71) Applicant: Ventrimend, Inc, Lake Forest, CA (US)

(72) Inventors: David Zarbatany, Lake Forest, CA (US); Randell Werneth, Lake Forest, CA (US)

(73) Assignee: Ventrimed Inc, Lake Forest, CA (US)

( * ) Notice: Subject to any disclaimer, the term of this patent is extended or adjusted under 35 U.S.C. 154(b) by 275 days.

(21) Appl. No.: 17/725,785

(22) Filed: Apr. 21, 2022

(65) Prior Publication Data

US 2022/0257955 A1 Aug. 18, 2022

Related U.S. Application Data

(63) Continuation of application No. 15/876,128, filed on Jan. 20, 2018, which is a continuation of application No. 13/368,685, filed on Feb. 8, 2012, now abandoned.

(60) Provisional application No. 61/441,627, filed on Feb. 10, 2011.

(51) Int. Cl.
*A61B 17/00* (2006.01)
*A61N 1/375* (2006.01)

(52) U.S. Cl.
CPC ........ *A61N 1/3756* (2013.01); *A61B 17/0057* (2013.01); *A61B 2017/00243* (2013.01); *A61B 2017/00592* (2013.01); *A61B 2017/00597* (2013.01); *A61B 2017/00601* (2013.01); *A61B 2017/00615* (2013.01)

(58) Field of Classification Search
CPC .... A61B 17/12122; A61B 2017/00597; A61B 2017/00615; A61B 2017/00632
See application file for complete search history.

(56) References Cited

U.S. PATENT DOCUMENTS

| | | | |
|---|---|---|---|
| 8,313,505 B2* | 11/2012 | Amplatz | A61B 17/12172 606/200 |
| 2001/0037129 A1* | 11/2001 | Thill | A61B 17/0057 606/213 |
| 2002/0035374 A1* | 3/2002 | Borillo | A61B 17/12172 606/194 |
| 2006/0122646 A1* | 6/2006 | Corcoran | A61B 17/0057 606/213 |

(Continued)

*Primary Examiner* — Martin T Ton  
(74) *Attorney, Agent, or Firm* — Michael R Shevlin

(57) ABSTRACT

Atrial appendage occlusion devices and cardiac monitoring positioned within the left atrial appendage and/or left atrium. In some embodiments the devices include an anchoring portion adapted to anchor the device in place adjacent the left atrial appendage, the anchoring portion comprising distal deformable anchoring portion adapted to be deployed in the left atrial appendage and a proximal deformable anchoring portion being adapted to be deployed in the left atrium, a barrier element secured to the anchoring portion and adapted to cover the left atrial appendage when implanted, and adapted to prevent blood clots from passing through the barrier element, and a cardiac monitoring element secured to at least one of the anchoring portions, the monitoring element including one or more sensors within in the left atrial appendage and/or left atrium and adapted to monitor left atrial cardiac data.

15 Claims, 20 Drawing Sheets

(56) References Cited

U.S. PATENT DOCUMENTS

2012/0172927 A1\* 7/2012 Campbell ........ A61B 17/12172
                                                    606/213
2013/0218192 A1\* 8/2013 Erzberger ........ A61B 17/12122
                                                    606/200

\* cited by examiner

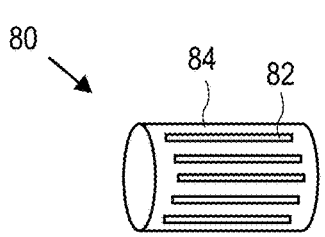
FIG. 7A
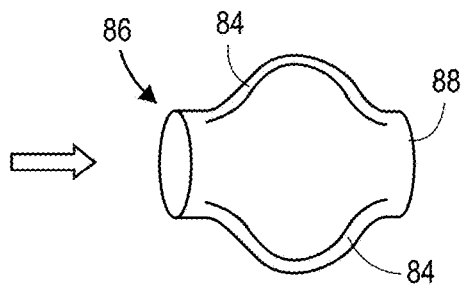
FIG. 7B
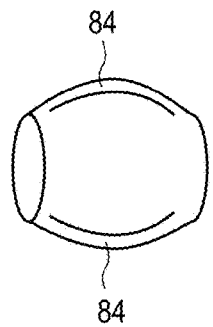
FIG. 7C
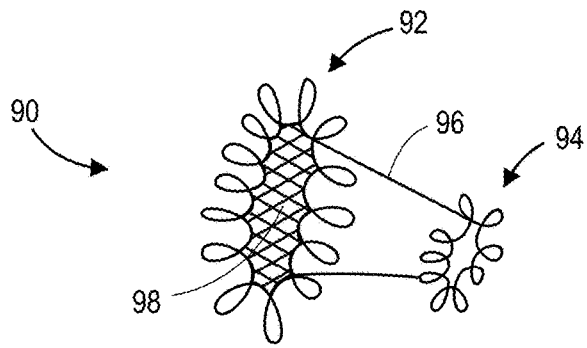
FIG. 8A
FIG. 8B
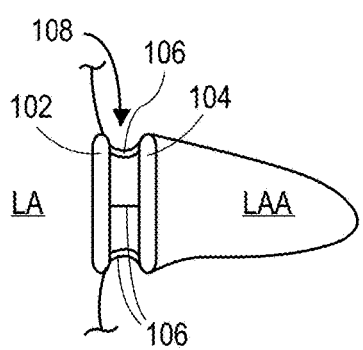
FIG. 9A
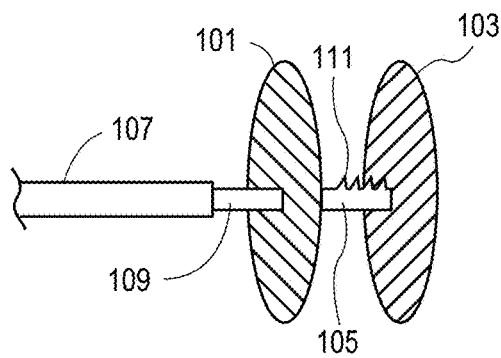
FIG. 9B

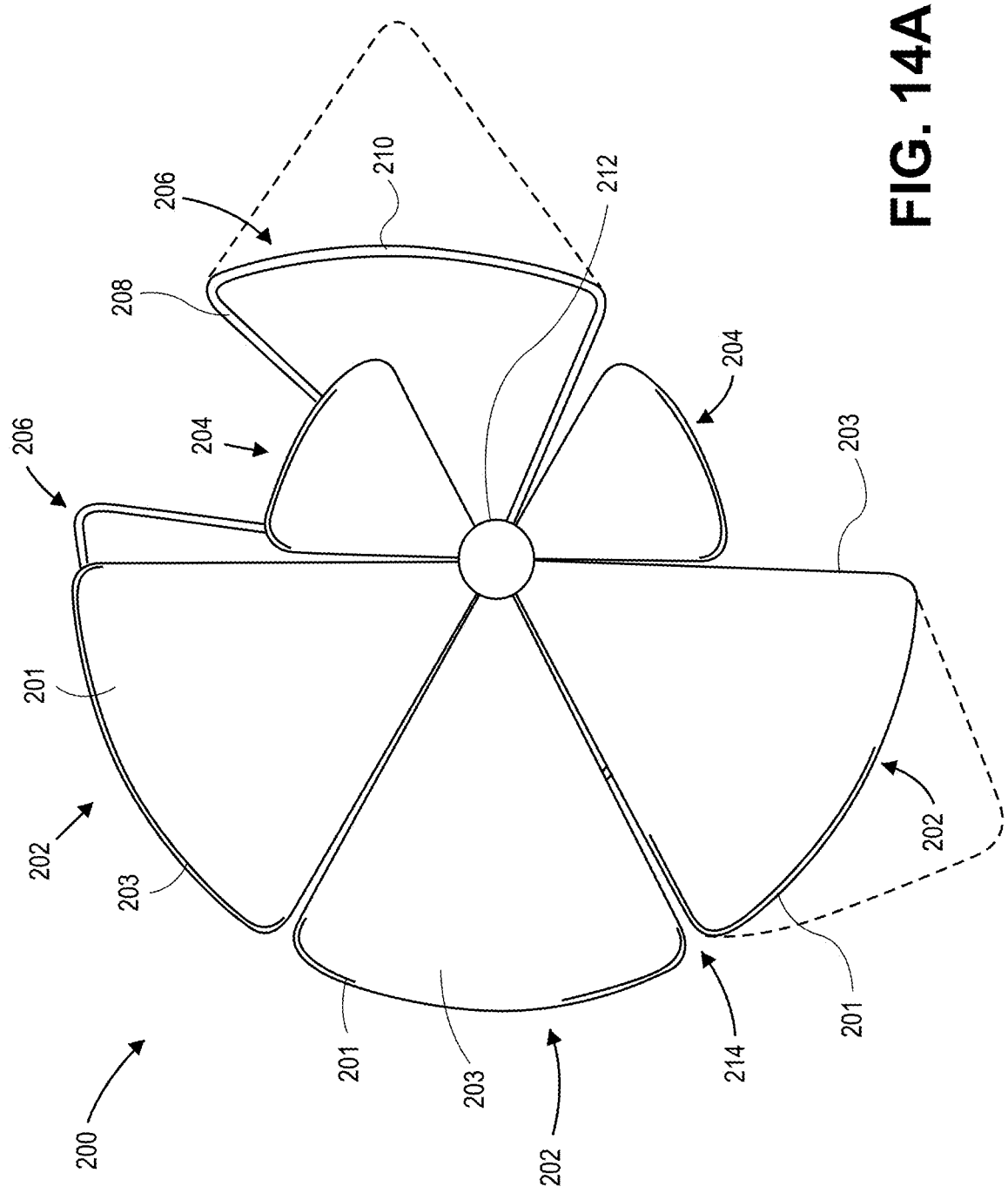

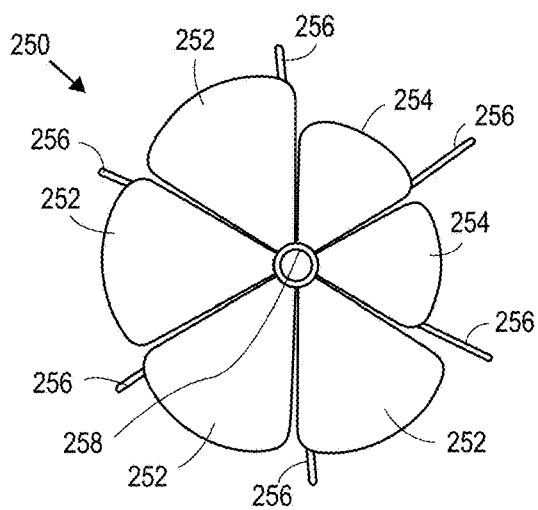
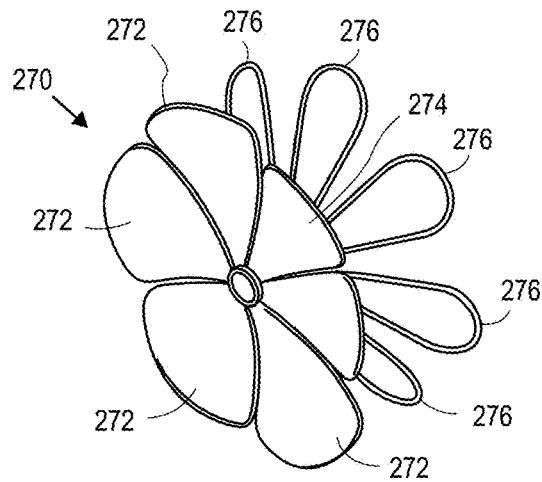
FIG. 15      FIG. 16A
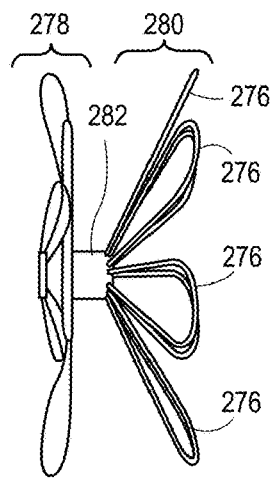
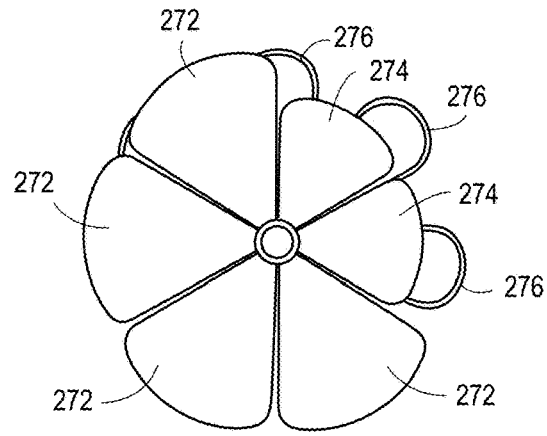
FIG. 16B      FIG. 16C
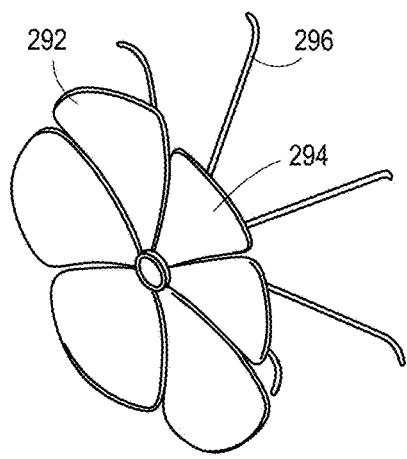
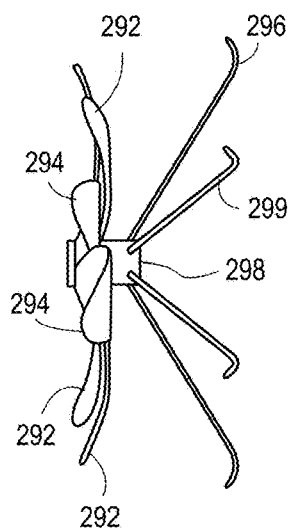
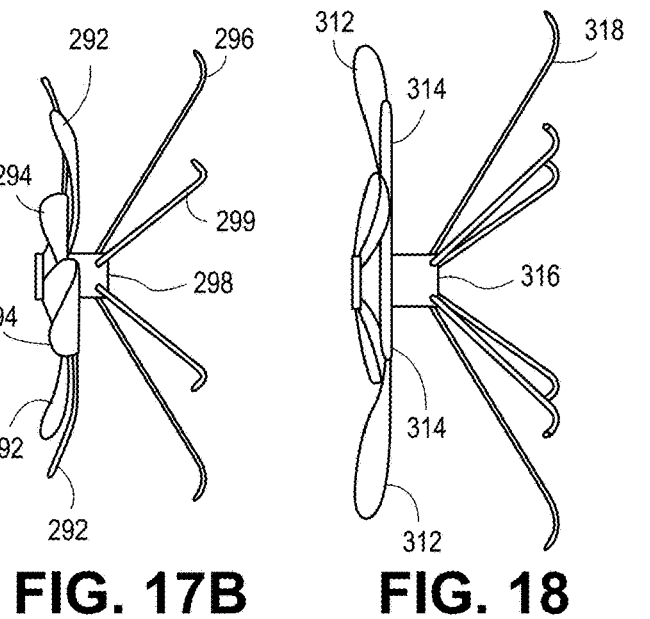
FIG. 17A      FIG. 17B      FIG. 18

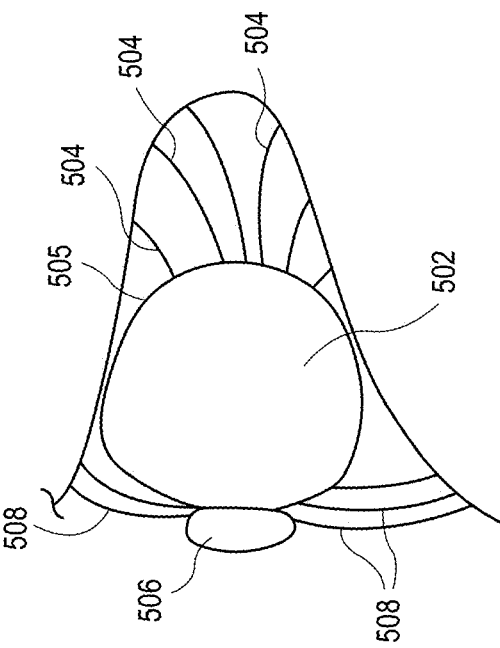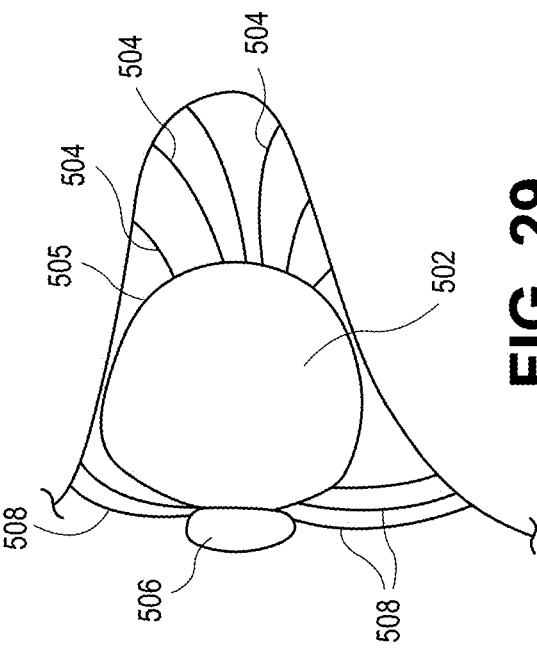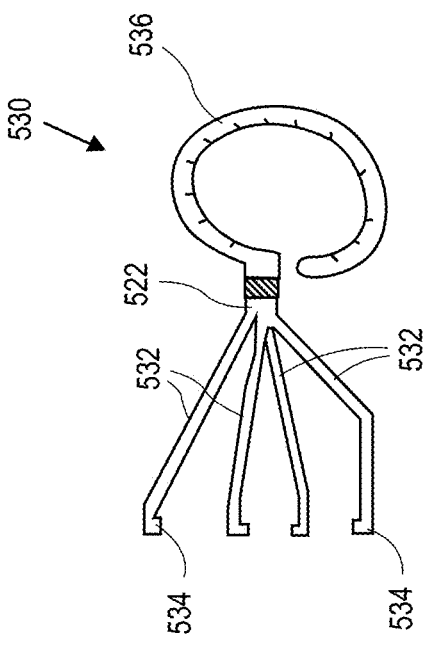

ATRIAL APPENDAGE OCCLUSION AND ARRHYTHMIA TREATMENT

CROSS REFERENCE TO RELATED APPLICATIONS

This application is a continuation application of U.S. patent application Ser. No. 15/876,128, filed Jan. 12, 2018, which is a continuation application of U.S. patent application Ser. No. 13/368,685, filed Feb. 8, 2012, which claims priority to U.S. Provisional Patent Application No. 61/441,627, filed Feb. 10, 2011, the entire disclosure of which is incorporated by reference herein.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE DISCLOSURE

Atrial fibrillation ("AF") is an arrhythmia of the heart that results in a rapid and chaotic heartbeat, producing lower cardiac output and irregular and turbulent blood flow in the vascular system. The left atrial appendage ("LAA") is a cavity extending from the lateral wall of the left atrium between the mitral valve and the root of the left pulmonary veins. The LAA normally contracts with the rest of the left atrium during a normal heart cycle, keeping blood from becoming stagnant therein, but often fails to contract with any vigor in patients experiencing AF due to the discoordinate electrical signals associated with AF. The result is that blood tends to pool in the LAA, which can lead to the formation of blood clots therein. The blood clots can then propagate out from the LAA into the left atrium. Since blood from the left atrium and ventricle supply the heart and brain, blood clots from the LAA can obstruct blood flow thereto, causing heart attacks, strokes, or other organ ischemia. Blood clots form in the LAA in about 90% of patients with atrial thrombus. Patients with AF account for one of every six stroke patients, and thromboemboli originating from the LAA are the suspected culprit in the vast majority of these cases. More than 3 million Americans have AF, which increases their risk of stroke by a factor of 5. Elimination or containment of thrombus formed within the LAA of patients with AF will significantly reduce the incidence of stroke in those patients.

Administering an anticoagulant such as warfarin is the most commonly prescribed treatment for stroke prevention in patients with AF. The effectiveness of warfarin, however, is challenged due to serious side effects, lack of patient compliance in taking the medication, a narrow therapeutic window, and an increased risk of bleeding.

LAA occlusion can be used as an alternative for patients who cannot use oral anticoagulants such as warfarin. Approximately 17% of patients cannot take anticoagulants because of a recent or previous bleeding, non-compliance, or pregnancy. Current US FDA-approved occlusion methods staple the LAA closed or suture and excise the appendage. Studies, however, have shown these techniques produce inconsistent results. Some new approaches, currently under FDA investigation, deliver an implant from within the vascular system.

Devices are needed, however, to more consistently and effectively prevent clots from entering the atrium from the appendage. While blocking the appendage from the atrium can prevent thrombus from entering the atrium, an approach that can also provide therapy for the arrhythmia will reduce the risk of stroke while treating the arrhythmia.

SUMMARY OF THE DISCLOSURE

One aspect of the disclosure is an implantable cardiac orifice occlusion device and cardiac monitoring device comprising: an anchoring portion adapted to anchor the device in place adjacent the left atrial appendage, a barrier element secured to the anchoring portion and adapted to cover the left atrial appendage when implanted, and adapted to prevent blood clots from passing through the barrier element, and a cardiac monitoring element secured to the anchoring portion, the monitoring element including one or more sensors positioned within in the left atrial appendage and/or left atrium adapted to monitor left atrial cardiac data.

In some embodiments the left atrial cardiac data includes at least one member of a group consisting of: electrical activity, blood pressure, pulse and ECG data.

In some embodiments the one or more sensors are configured to acquire data to calculate and/or determine at least one member of a group consisting of: AF burden, left atrial pressure, temperature, transthoracic impedance, impending atrial fibrillation and impending ventricular fibrillation.

In some embodiments the monitoring element further comprises circuitry configured to process the monitored data.

In some embodiments the monitoring element is configured to monitor data over time.

In some embodiments the cardiac monitoring element is adapted to store the data and/or wirelessly transmit the data to an external device.

In some embodiments the cardiac monitoring element may continuously transmit the data to the external device and/or receive a signal from an external device.

In some embodiments further comprising a treatment element adapted to provide at least one treatment selected from a group consisting of: treating an arrhythmia, pacing cardiac tissue, and delivering a therapeutic agent.

In some embodiments the treatment element is a drug delivery device adapted to deliver a drug or other agent into the left atrium and/or left atrial appendage.

In some embodiments the anchoring portion, the barrier element, and the cardiac monitoring element are integrated into a singular implantable device.

In some embodiments the anchoring portion comprises a distal deformable anchoring portion and a proximal deformable anchoring portion, the distal anchoring portion adapted to be deployed in a left atrial appendage and anchored to left atrial appendage tissue, wherein the proximal anchoring portion is adapted to be deployed in a left atrium and anchored to left atrial tissue.

One aspect of the disclosure is an implantable cardiac orifice occlusion device and cardiac monitoring device positioned within the left atrium and/or left atrial appendage, comprising: an anchoring portion adapted to anchor the device in place adjacent the left atrial appendage, a barrier element secured to the anchoring portion and adapted to cover the left atrial appendage when implanted, and adapted to prevent blood clots from passing through the barrier element, a cardiac monitoring element secured to the anchoring portion configured to monitor left atrial cardiac data, the monitoring element comprising one or more sensors within in the left atrial appendage and/or left atrium and adapted to monitor left atrial cardiac data; and circuitry configured to process the monitored data, wherein the cardiac monitoring element being further adapted to store the data and/or wirelessly transmit the data to an external device.

In some embodiments the data includes at least one member of a group consisting of: electrical activity, blood pressure, pulse and ECG data.

In some embodiments the cardiac monitoring element is further configured to calculate and/or determine from the acquired data at least one member of a group consisting of: AF burden, left atrial pressure, temperature, transthoracic impedance, impending atrial fibrillation and impending ventricular fibrillation.

In some embodiments the cardiac monitoring element is further adapted to receive a signal from an external device.

In some embodiments the anchoring portion comprises a distal deformable anchoring portion and a proximal deformable anchoring portion, the distal anchoring portion adapted to be deployed in a left atrial appendage and anchored to left atrial appendage tissue, wherein the proximal anchoring portion is adapted to be deployed in a left atrium and anchored to left atrial tissue.

One aspect of the disclosure is a method of cardiac orifice blocking and cardiac monitoring using left atrial cardiac data, comprising providing an integrated implantable device comprising an anchoring portion, a barrier element, and a cardiac monitoring element, anchoring the anchoring portion against cardiac tissue near a left atrial appendage to block the flow of clots through the orifice with the barrier element, positioning one or more sensors of the cardiac monitoring element within the left atrial appendage and/or left atrium to monitor left atrial cardiac data, wherein the data includes at least one member of a group consisting of: electrical activity, blood pressure, pulse and ECG data.

In some embodiments the method further comprises wirelessly transmitting the patient data to an external device.

In some embodiments the method further comprises circuitry configured to process the monitored patient data, wherein the method further comprises.

In some embodiments the method further comprises a treatment element providing at least one treatment selected from a group consisting of: treating an arrhythmia, pacing cardiac tissue, and delivering a drug or therapeutic agent.

BRIEF DESCRIPTION OF THE DRAWINGS

Exemplary patentable features of the disclosure are set forth in the claims. A better understanding of the features and advantages of the present disclosure will be obtained by reference to the following detailed description that sets forth illustrative embodiments, in which the principles of the disclosure are utilized, and the accompanying drawings of which:

FIGS. 7A-7C illustrate an exemplary embodiment in which one or more of the anchors is made from a tubular element in which portions of the tube are removed to creates slots therein.

FIGS. 8A and 8B illustrate an exemplary embodiment of an implant that can occlude the left atrial appendage.

FIGS. 9A-B illustrate an exemplary embodiment in which the implant comprises a first anchor and a second anchor that are adapted to clamp down on the tissue at the ostium of the left atrial appendage.

FIGS. 14A-C illustrate an exemplary embodiment of a left atrial appendage occlusion implant.

FIG. 15 illustrates a front view of an exemplary embodiment of an occlusion implant.

FIGS. 16A-C illustrate an exemplary embodiment of an occlusion implant.

FIGS. 17A-B illustrate an exemplary embodiment of an occlusion implant.

FIG. 18 illustrates a side view of an exemplary embodiment of an occlusion implant.

FIG. 28 illustrates an alternative embodiment of an implant.

FIG. 29 illustrates a further exemplary embodiment of an implant.

FIG. 30 illustrate an exemplary embodiment in which the implant includes a plurality of expanding arms coupled to a hub.

DETAILED DESCRIPTION

The disclosure herein relates to isolating clots to prevent them from entering into an atrium of the heart. While the disclosure focuses on the left atrial appendage ("LAA") and the left atrium, the systems can be used in the right atrial appendage and the right atrium. The devices may also be used to close other undesirable orifices in the heart, such as Atrial Septal Defects ("ASD") or Patent Foramen Ovales ("PFO"). They may also be used in other portions of a body unrelated to the heart. The disclosure herein also relates to providing therapy for a detected cardiac arrhythmia to attempt to prevent the formation of clots within the appendage.

One aspect of the disclosure herein relates to LAA occlusion devices and methods of use. A second aspect of the disclosure herein provides for intra-atrial or intra-LAA cardiac monitoring and therapy for a detected arrhythmia.

The first aspect can be a stand-alone procedure to occlude the LAA from the left atrium. The second aspect can similarly be a stand-alone procedure to monitor and provide therapy. Alternatively, the occlusion device can be integrated with the therapy aspect. When combined, the occlusion device can be separate and distinct from the monitoring and therapy components, or they can be combined into an integrated device.

Figure 1:
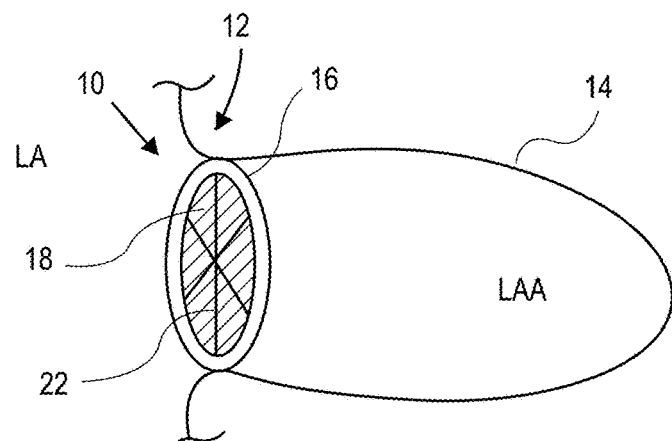
FIG. 1 illustrates an exemplary embodiment of a device adapted to prevent clots from entering the left atrium from the left atrial appendage.

FIG. 1 illustrates an exemplary embodiment of a device adapted to prevent clots from entering the left atrium from the LAA. FIG. 1 shows a perspective view of device 10 in a deployed configuration and position blocking off fluid communication between a left atrium ("LA") and a left atrial appendage ("LAA"). Implant 10 has been deployed adjacent ostium 12 to the LAA, engaging a portion of LAA wall 14. Implant 10 includes an anchoring element 16, shown with a generally annular shape. Secured to anchoring element 16, either directly or indirectly, is barrier 18.

Barrier 18 acts as a primary barrier preventing blood from flowing into the LAA from the LA. Barrier 18 can be any suitable material to prevent blood flow into the LAA, such as, for example, expanded PTFE, PTFE, woven polyester fabric, biocompatible materials, polyurethane membrane, etc. In FIG. 1, barrier 18 is secured directly to anchoring element 16, such as by adhesive or stitching with suture material. Barrier 18 can be reinforced by frame 22, which in this embodiment includes a plurality of elongate elements. The elongate element(s) are secured to anchoring element 16 and optionally to barrier, extending across the face of barrier 18 to reinforce the barrier. The frame can be, for example, one elongate element extending across the face of barrier 18, while it can also be a plurality of interconnected elongate elements. Other configurations are within the scope of the disclosure. For example, the frame can be a plurality of braided wires. The frame can be secured to the distal side of barrier 18, or it can be disposed proximally to barrier 18.

In alternative embodiments barrier 18 acts as a filter, allowing some blood components to flow into and out of the LAA but preventing clots from flowing from the LAA into the LA. That is, barrier 18 can have a porosity to allow some blood components to flow therethrough while preventing clots (or other non-clot blood components) from passing therethrough. In some embodiments the pores can be from, for example, about 60 microns to about 150 microns in diameter. These pores sizes are not intended to be limiting.

The anchoring element is adapted to anchor implant 10 in place within the LAA. Anchoring element 16 is shown as a generally annularly-shaped component, but can have a variety of shapes. Anchor 16 provides the expansion force needed to anchor implant 10 in place. The anchor can be made from a shape memory material such as nitinol, allowing it to be deformed into a delivery configuration to deliver it to the target location. Upon release from a delivery sheath or catheter, the anchor reverts to its memory configuration. The memory configuration can be adapted to secure the anchor in place based on the outwardly directed force from the anchor against the tissue. In some embodiments the radial expansion force is applied by constructing the device from a shape memory material such as, for example, nickel-titanium (nitinol).

Figure 2:
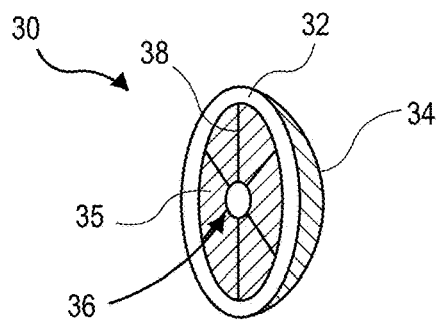
FIG. 2 illustrates an exemplary embodiment of an implant adapted to prevent clots from entering the left atrium from the left atrial appendage.

FIG. 2 illustrates an exemplary embodiment of an implant adapted to prevent clots from entering the left atrium from the LAA. Implant 30 includes anchor 32, frame 38, delivery element 36, and barrier 35. Anchor 32 can be similar to anchor 16 in FIG. 1, and frame 38 can be similar to frame 22. Implant 30, in addition to barrier 35, includes secondary barrier 34, which is coupled to the distal portion of anchor 32, and is disposed further distally than barrier 35. Barrier 34 acts as a secondary barrier to blood flow that prevents blood flow into the LAA. Barrier 34 can be made from any suitable material to occlude the flow of blood, such as, for example without limitation, PTFE. Delivery element 36 is adapted to be releasably coupled to a delivery tool (not shown), allowing implant 30 to be positioned using the delivery tool and released therefrom when desired. In alternative embodiments, implant 30 need not have barrier 35, and only barrier 34 is included in implant 30 to block off the LAA from the left atrium. Additionally, barrier 34 can be taught relative to anchor 32 such that it does not extend distally relative to anchor. In some embodiments barrier 34 and 35 can be made from the same material and essentially form a 2-ply barrier.

Figure 3:
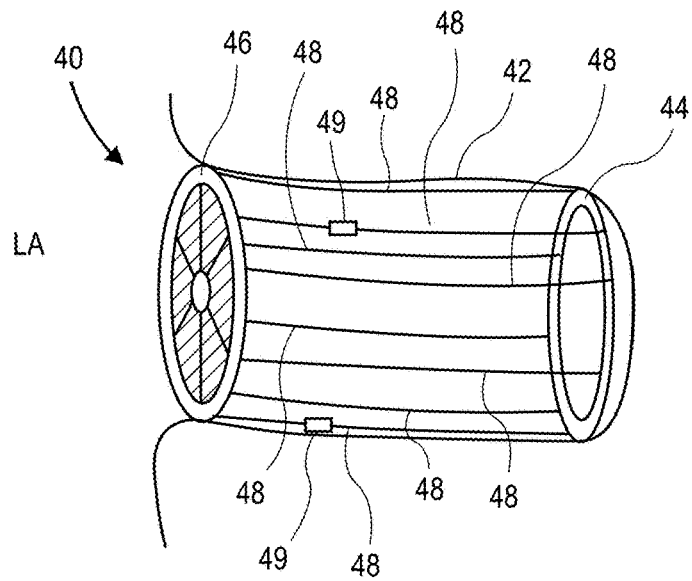
FIG. 3 illustrates an exemplary embodiment of an implant to prevent clots from entering the left atrium from the left atrial appendage.

FIG. 3 illustrates an exemplary embodiment of an implant to prevent clots from entering the left atrium from the LAA. Implant 40 includes a first anchor 46, which can be similar to the anchoring elements shown in FIGS. 1 and 2. Implant 40 also includes anchoring element 44 which is deployed towards the distal end of LAA 42. Anchoring element 44 is coupled to anchoring element 46 with struts 48. The struts are coupled to the anchoring elements at a plurality of locations around the annularly-shaped elements. One or more of struts 48 can optionally have electrodes 49 disposed thereon, which can be adapted to monitor cardiac activity and pace cardiac tissue, which is described in more detail herein. Anchor 44 can be biased to expand to a deployed configuration with a larger diameter than the section of the LAA in which it is deployed. Anchor 44, as shown, therefore applies an outwardly directed force on the LAA to help secure it, and the rest of implant 40, in place.

Figure 4A:
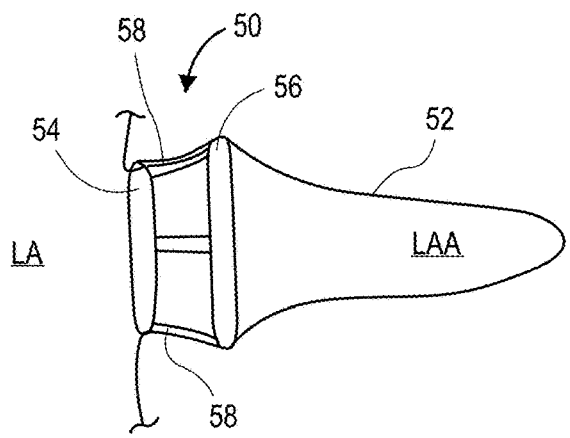
FIGS. 4A-4E illustrate an exemplary embodiment of an implant adapted to prevent blood flow into the left atrial appendage.
Figure 4B:
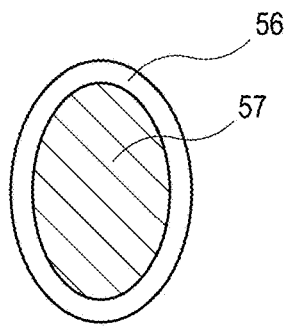
Figure 4C:
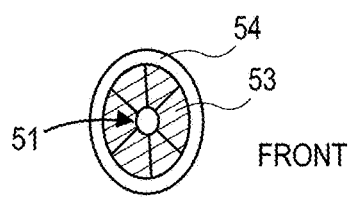
Figure 4D:
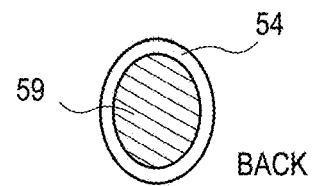
Figure 4E:
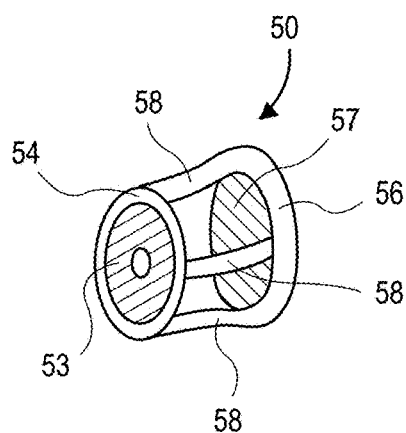

FIGS. 4A-4E illustrate an exemplary embodiment of an implant adapted to prevent blood flow into the LAA. Implant 50 includes proximal anchor 54, distal anchor 56, and interconnecting therapy elements 58. Anchor 54 is disposed at the ostium, or just outside the ostium of the LAA. The length of therapy elements 58 can be adjusted, but in this embodiment anchor 56 is shown deployed closer to the ostium than to the distal end of the LAA. FIG. 4B illustrates a front view (looking distally) of distal anchor 56, wherein anchor 56 is coupled to optional barrier 57. Anchor 56 and barrier 57 can be similar to other anchors and barriers described herein. FIG. 4C illustrates a front view of proximal anchor 54, with optional barrier 53. Also shown is delivery element 51 which is adapted to releasably couple to a delivery tool (not shown). Barrier 53 does not extend across the delivery element 51. FIG. 4D illustrate a back view (looking proximally) of anchor 54, wherein an optional additional barrier layer 59 is secured to anchor 54. FIG. 4E illustrates a perspective view of implant 50 (LAA not shown), illustrating a plurality of therapy elements 58 extending from anchor 54 to anchor 56. Barriers to prevent the flow of blood are also shown.

Figure 5:
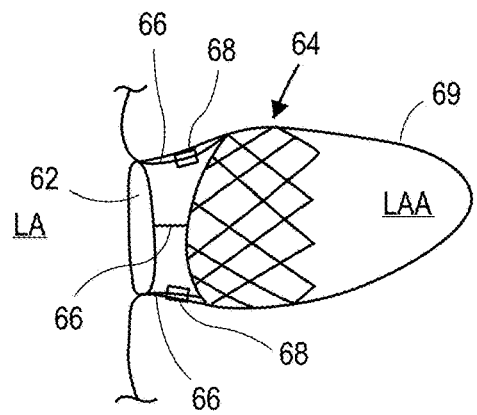
FIG. 5 illustrates an exemplary embodiment of an occlusion implant.
Figure 6:
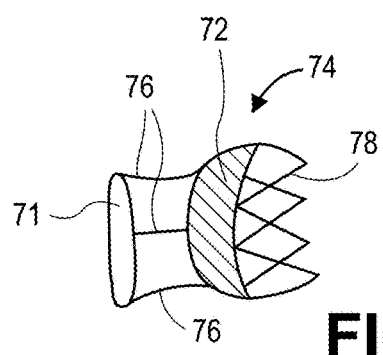
FIG. 6 illustrates a variation on the embodiment in FIG. 5 in which the device includes a barrier secured to an expandable anchor.

FIG. 5 illustrates an exemplary embodiment of an occlusion implant. Implant 60 includes a first anchor 62 connected to a second, distal, anchor 64. Distal anchor 64 resembles a traditional stent-like design, and can be made from shape memory material as is known in the art. The anchors are connected by connectors 66, which can have electrodes 68 secured thereto for monitoring and/or pacing as described herein. Distal anchor 64 is expanded in the LAA distal to the ostium to anchor implant 60 securely in place, while anchor 62 is expanded closer to the ostium (either just inside or just outside the ostium). Anchor 62 can include a barrier layer as described herein to prevent blood flow into the LAA and to prevent clots from exiting the LAA. FIG. 6 illustrates a variation on the embodiment in FIG. 5 in which the device includes barrier 72 secured to expandable anchor 78, which is in the form of an expandable lattice of material. The implant also includes anchor 71 secured to anchor 74 with connectors 76, which can have electrodes secured thereto (not shown).

FIGS. 7A-7C illustrate an exemplary embodiment in which one or more of the anchors is made from a tube in which portions of the tube are removed to creates slots therein. FIG. 7A illustrates tubular element 80 in which material has been removed to form slots 82 therein. By removing material, a plurality of struts are formed extending from the proximal portion to the distal portion. The tube can be cut by, for example without limitation, laser cutting techniques or etching a nitinol tubular element. After the slots are cut in the tubular element, the struts can be heat set in a desired memory configuration. For example, FIG. 7B illustrates struts 84 (only one shown) in an expanded configuration in which a center region expands outwardly to a greater diameter than the distal and proximal ends of the struts. The ends of the tubes create proximal anchor 86 and distal anchor 88, although the tube can be attached to additional proximal and distal anchors, such as those described herein. FIG. 7C illustrates an exemplary expanded configuration in which struts 84 have a smoother curve than the configuration in FIG. 7B. The force of the struts expanding to their memory configuration locks the implant in place. While straight cuts are shown in FIG. 7A, a variety of types of cuts can be made in the tubular element. For example without limitation, helical cuts can be made in the tube. The pattern, width, orientation, etc., of the cuts can be varied, even along the length of the tubular element, to provide for an expandable configuration with select properties.

FIGS. 8A and 8B illustrate an exemplary embodiment of an implant that can occlude the LAA. Implant 90 is a continuous wire form, formed from a single wire. The wire forms proximal anchor 92, distal anchor 94, and connects the anchors with sections 96. Implant 90 also includes barrier 98 adapted to prevent blood flow into or out of the LAA. Distal anchor 94 is secured in the LAA to secure the implant in place, while anchor 92 is adapted to expand near the ostium such that barrier 98 blocks the flow of blood into LAA. FIG. 8B illustrates a side view of implant 90.

FIGS. 9A-B illustrate an exemplary embodiment in which the implant comprises a first anchor and a second anchor that are adapted to clamp down on the tissue at the ostium of the LAA. The two anchors are positioned on opposite side of the ostium tissue, and once positioned can revert to a closed configuration, clamping down on the tissue. The clamping action secures the implant in place and helps provide a seal around the periphery of the implant. The proximal anchor can include one or more barrier layers as set forth herein to prevent blood into the LAA. FIG. 9A illustrates implant 100 comprising proximal anchor 102 and distal anchor 104 connected by elements 106. In their deployed positions, they are clamped securely around tissue 108 at the ostium of the LAA. FIG. 9B illustrates an alternative concept in which the distance between anchors 101 and 103 can be adjusted by actuation with delivery device 107. Delivery device 107 can retract actuation element 109 proximally, causing teeth 111 to ratchet with respect to proximal anchor 101. Once the tissue at the ostium (not shown) is sufficiently clamped between the anchors, the delivery device can be released from actuation element 109. At least one of the anchors can have a barrier, as shown, to prevent the flow of blood into the LAA.

In any of the embodiments above, the proximal anchor (closer to the atrium) can be thin and have a fabric covering on most of the anchor but not the entire anchor. The uncovered portion of the anchor allows for cardiac monitoring and and/or pacing as described herein. The inner, or distal, disk can be mostly covered by a fabric.

Figure 10:
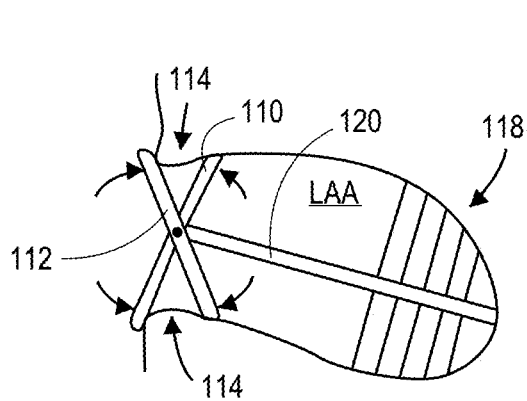
FIG. 10 illustrates an exemplary embodiment of an implant with a ratcheting design to secure a portion of the implant in place.

FIG. 10 illustrates an exemplary embodiment of an implant with a ratcheting design to secure a portion of the implant in place. The implant includes arms 110 and 112 connected to expandable anchor 118 with connector 120. The proximal portions of the arms are positioned to be engaging the atrium, as shown. The distal portions are positioned to be inside the LAA, as shown. Once in their respective positions, the arms are actuated towards one another in the direction of the arrows shown in the figure. This clamps tissue 114 between the arms, securing the implant in place. The arms can also be adapted with locking features, such that when engaged they will lock the arms in a locked configuration. Expandable anchor 118 can be of any suitable anchor that can be deployed in the LAA and secured against tissue. Once the arms are moved to their clamped configurations, the blood is blocked from flowing into the LAA. There may optionally be a barrier layer material secured to the arms, and adapted such that as the arms are closed towards one another, the barrier occludes the flow of blood into the LAA.

Figure 11:
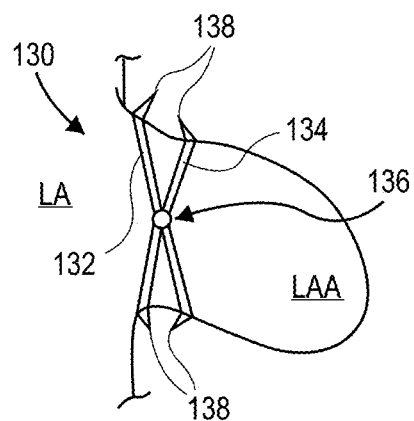
FIG. 11 illustrates an alternative ratcheting embodiment.

FIG. 11 illustrates an exemplary embodiment of a portion of implant 130 (distal anchor in LAA not shown) includes ratcheting arms similar to FIG. 10. Arms 132 and 134 include tissue piercing elements 138 adapted to pierce through tissue near the ostium to help more securely anchor arms in place. Implant 130 also includes delivery element 136 which is adapted to releasably couple to a ratcheting mechanism of the delivery system to actuate the arms between open and closed positions.

Figure 12:
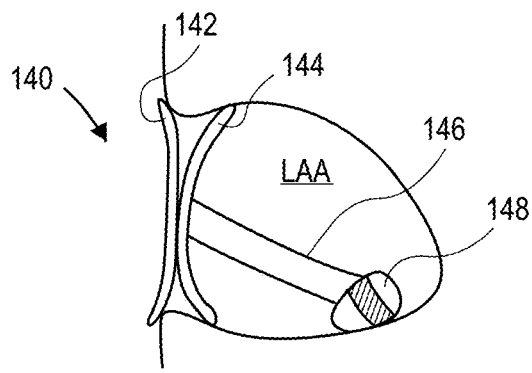
FIG. 12 illustrates an implant with arms connected to a distal anchor adapted to monitor and/or treat tissue.

FIG. 12 illustrates implant 140 with arms 142 and 144 connected to distal anchor 148 with connector 146. Distal anchor 148 is adapted to be in contact with LAA tissue as shown to monitor and/or pace tissue as described herein.

Figure 13A:
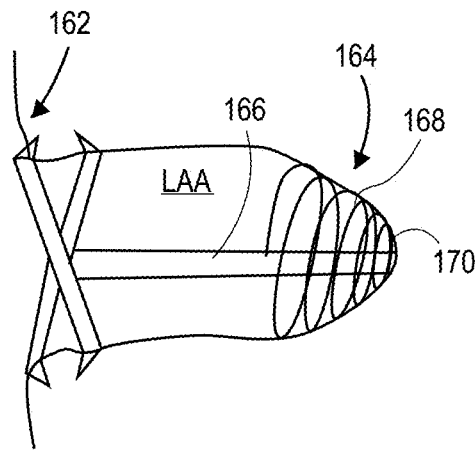
FIGS. 13A-13D illustrate an exemplary embodiment in which the distal appendage anchor has a general conical expanded configuration.
Figure 13B:
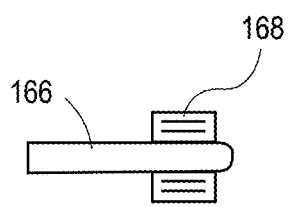
Figure 13C:
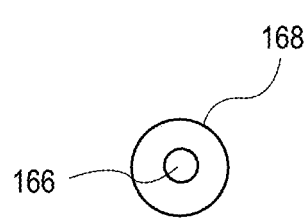
Figure 13D:
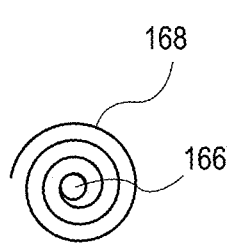

FIGS. 13A-13D illustrate an exemplary embodiment in which the distal appendage anchor has a general conical expanded configuration. The general conical configuration more closely resembles the natural contours of the LAA and can more easily be anchored in place within the LAA. Implant 160 includes ratcheting proximal anchor portion 162, as described herein, distal expandable anchor 168, and connector 166. FIG. 13B illustrates a side view of a portion of the implant showing the expandable anchor in a collapsed delivery configuration. FIG. 13C shows an end-view of the same configuration. FIG. 13D shows an end-view of the distal anchor in an expanded configuration. Distal anchor 164 has a general conical shape tapering towards the distal end of the implant. The anchor is made from a single wire secured to connector, but in other embodiments more than one wire can be used and different configurations of the anchor can be used.

Figure 14B:
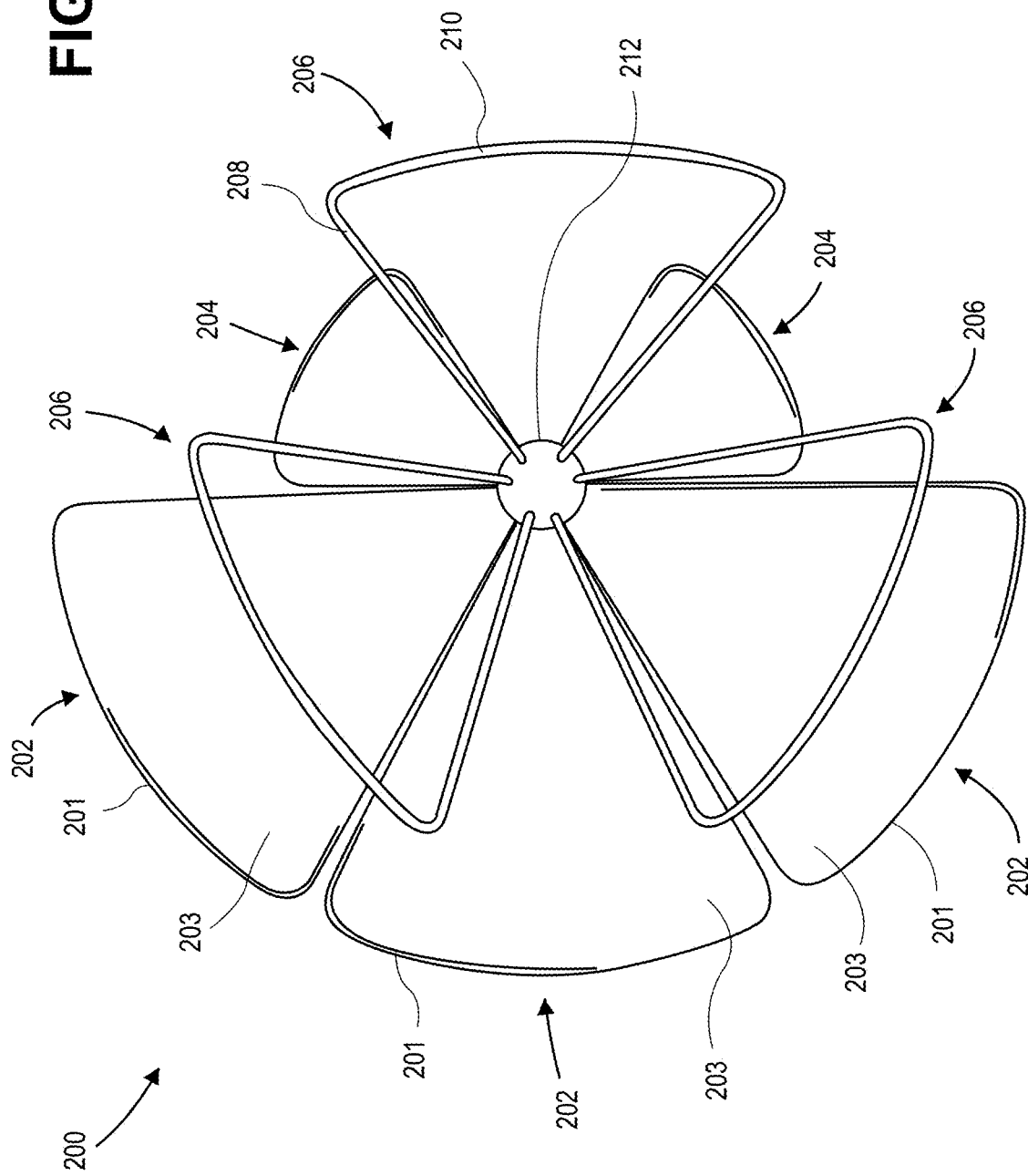
Figure 14C:
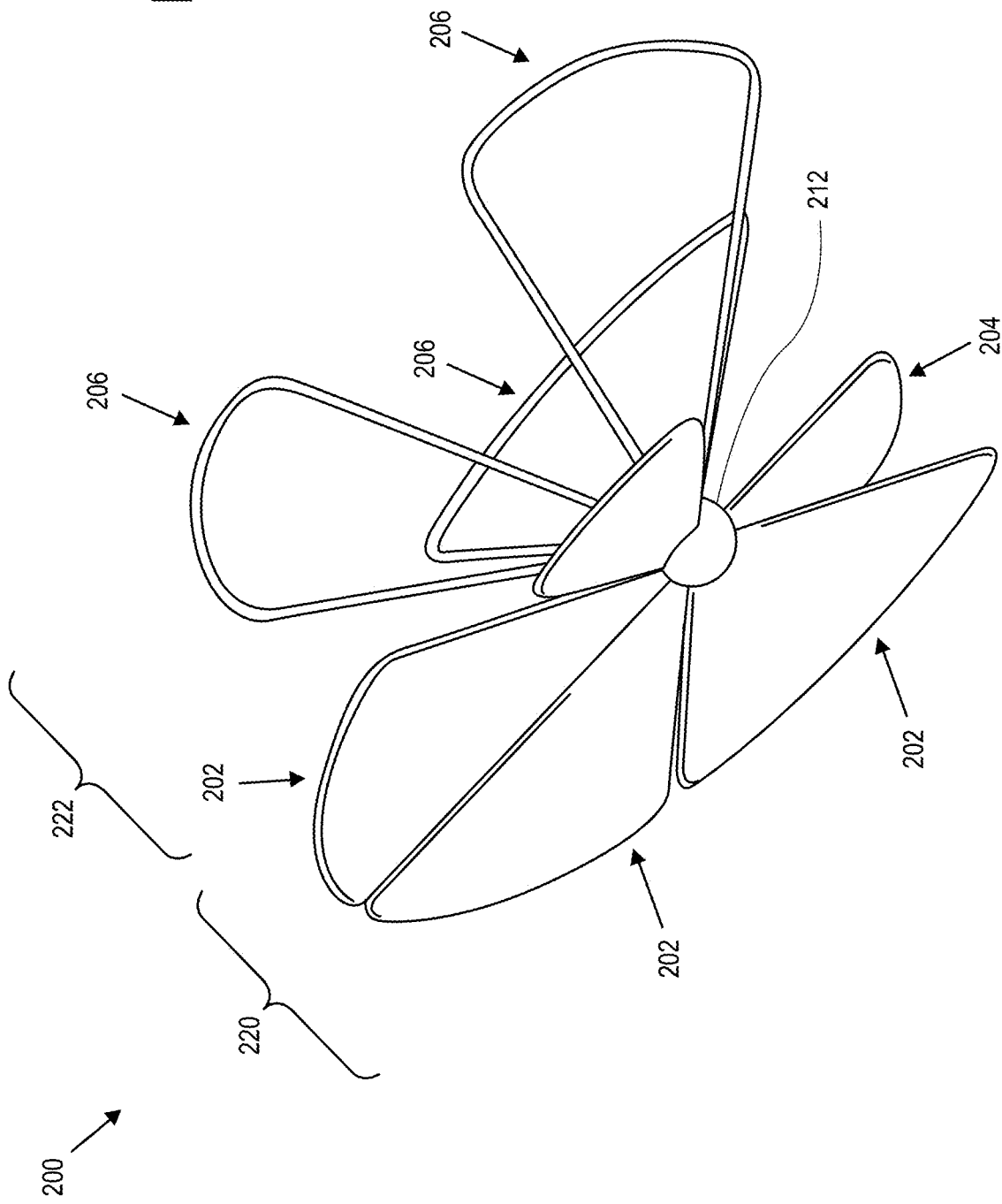
Figure 14D:
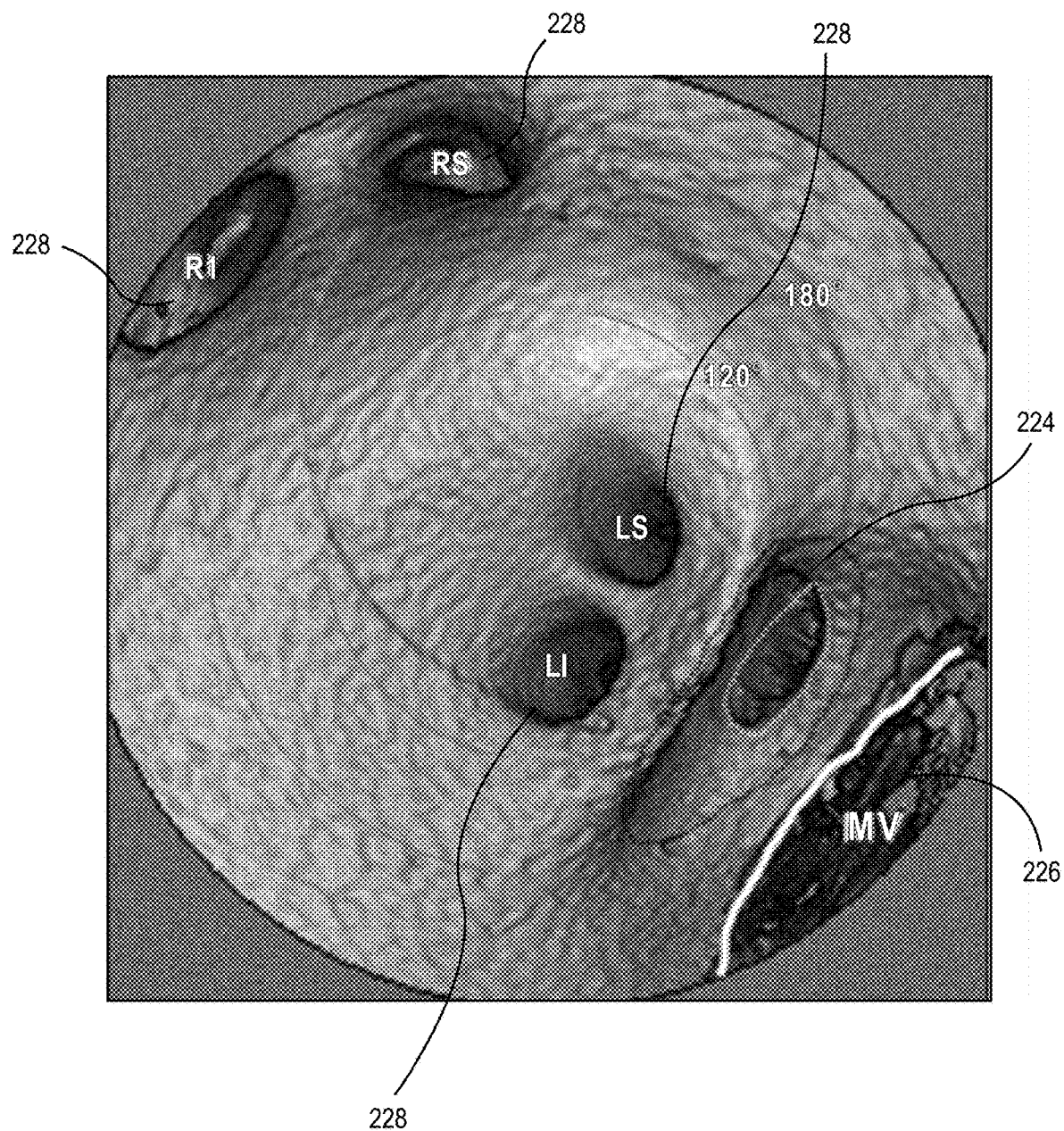
FIG. 14D illustrates a portion of a left atrium, illustrating the relative positions of left atrial appendage ostium, mitral valve, and left pulmonary veins ostia.

FIGS. 14A-C illustrate an exemplary embodiment of a LAA occlusion implant. FIGS. 14A-C illustrate a front view (distally facing), a rear view (proximally facing), and a perspective view, respectively. Implant 200 includes a proximal portion 220 (see FIG. 14C) and a distal portion 222. Proximal portion 220 includes leaflets, or blades, 202 and 204, each having a generally triangular shape. In some embodiments they have a generally elliptical shape. Once deployed, the leaflets are adapted to engage a portion of the atrial wall. FIG. 14D illustrates a portion of a left atrium, illustrating the relative positions of LAA ostium 224, mitral valve 226, and left pulmonary veins ostia 228. The mitral valve and ostia to the pulmonary veins are relatively close to the LAA ostium, and as such any implant positioned in the left atrium must not obstruct the flow of blood through the mitral valve or the pulmonary veins. Leaflets 202 are larger than leaflets 204. Leaflets 204 are aligned with the mitral valve 226 and pulmonary veins ostia 228, respectively, and are sized such that they do not obstruct the flow of blood therethrough. Leaflets 202 are not disposed such that they would block the flow of blood through the ostia 228 or mitral valve 226 (or any other structure), and as such they can be larger than leaflets 204. In general, any leaflets facing the posterior and superior walls can be longer than leaflets extending towards the mitral valve and pulmonary veins to provide for more surface contact with the atrial wall. Additionally, the leaflets that extend towards the pulmonary veins can be slightly curved into the base of the pulmonary veins.

Leaflets 202 each comprise a frame element 201 and a barrier 203. Leaflets 204 are similarly designed. Frame elements 201 have a general triangular or elliptical shape, and each has two ends secured to hub 212. Frame elements 201 can be, for example, wire made from, for example, nitinol. Nitinol, or other material with shape memory and/or superelastic properties, allows the triangular wire form to be deformed for loading into a delivery system, with the wire form converting to the triangular shape upon deployment due to the shape memory and/or superelastic properties of the nitinol.

Figure 36A:
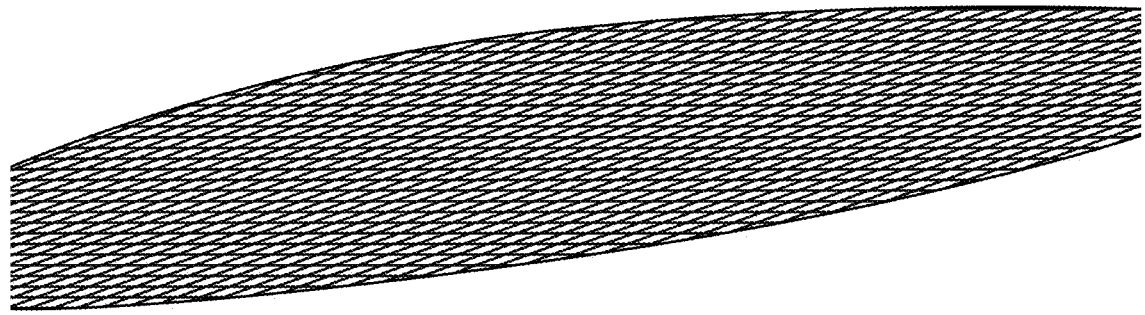
FIGS. 36A and 36B conceptually illustrate a frame element that includes one or more braided elements.
Figure 36B:
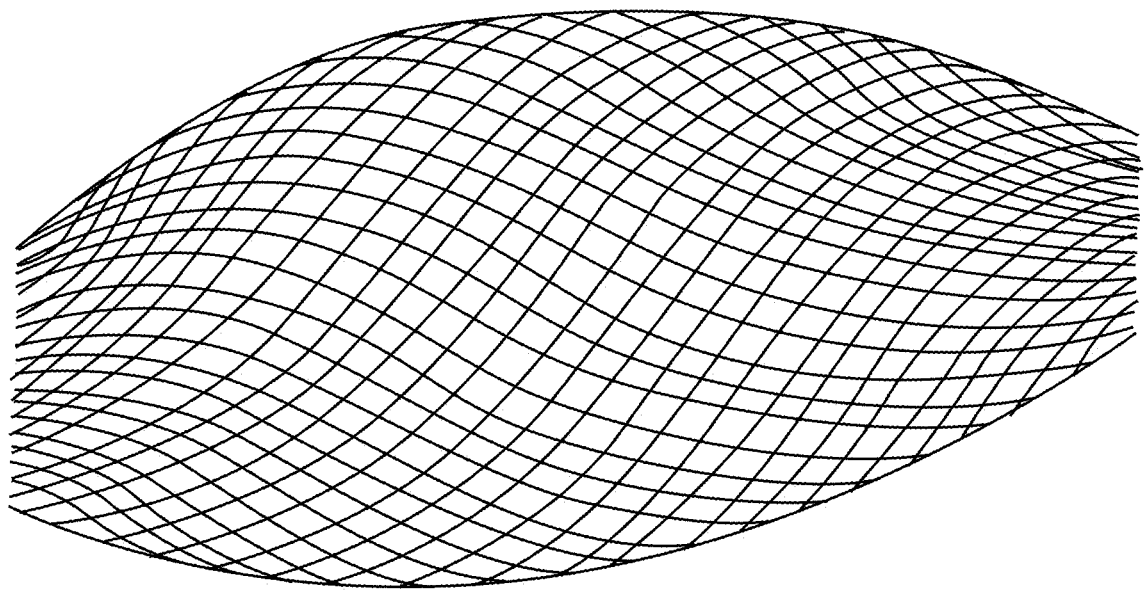

FIGS. 36A and 36B conceptually illustrate a frame element that includes one or more braided elements. In this specific embodiment the frame element is a braided nitinol wire that is heat set into the deployed configuration shown in FIG. 36B. More than one wire can be used as well. The braided pattern allows the frame element to be lengthened into a reduced radial dimension for loading, as shown in FIG. 36A. The braided frame element is adapted to then expand in radial dimension upon deployment from a delivery device through shortening the axial length, as shown in FIG. 36B. The frame element would be secured to a barrier, such as any of the barriers described herein.

Distal portion 222 includes a distal anchor, which in this embodiment comprises a plurality of anchors 206. Anchors 206 are similar in shape to the frame elements 201 from leaflets 202 and 204. Anchors 206 can be made from a wire, and can be made from, for example, nitinol. Each anchor wire has two ends secured to hub 212, to which leaflets 202 and 204 are also secured. The components can be secured to hub 212 with any suitable technique, such as bonding, welding, etc. Anchors 206 are adapted to expand and anchor in the LAA to secure the implant in place. Any of the distal anchors described herein can be used as the distal portion of implant 200. Also, while three anchors 206 are shown, any suitable number of anchors can be incorporated into implant 200. Additionally, shapes other than the generally triangular shape can be used. For example, anchors 206 can have four sides rather than three.

Leaflets 202 and 204, and anchors 206 are adapted to be collapsed down into delivery configurations such that they can be delivered endoluminally to a target location within the heart. In one exemplary embodiment, the radially outer portions of leaflets 202 are adapted to collapse downward and in the proximal direction towards one another such that the leaflets are adapted to be disposed within a delivery catheter, sheath, or other delivery instrument. The leaflets can be secured to hub such that as they collapse they overlap one another into a staggered orientation, easing their collapse. A central portion of frame elements 201 of each of the leaflets can additionally be adapted to bend outward to ease in the collapse of frame 201 (shown in phantom on one leaflet in FIG. 14A). Barriers 203 can have slack built into them so that frames 101 can collapse. Upon their release from the delivery instrument, leaflets will revert to their memory configuration shown in FIGS. 14A-C due to, for example, shape memory properties of frames 101. Similarly, anchors 206 are adapted to collapse into a delivery configuration. Anchors 206 collapse distally and inward towards one another. A central portion of wires 210 can be adapted to bend along a predetermined location to assist in the collapse of anchors 206 (shown in phantom for one of the anchors 206 in FIG. 14A). As such, when the proximal portion and distal portions of implant are collapsed, the proximal portion extends generally proximally from hub 212, and the distal portion extends generally distally from hub 212. The large leaflets can additionally optionally act as cardiac monitoring and pacing electrodes as described below. Additionally, the frames of the proximal blades and distal anchors can have electrodes mounted thereon.

FIG. 15 illustrates a front view of an exemplary embodiment of an occlusion implant. The design is similar to the design in FIGS. 14A-C, and therefore not every feature will be described. Implant 250 includes four larger blades 252 and two smaller blades 254. There is less space between blades 254 than in the design in FIGS. 14A-C. Blades 254 are similarly sized such that they don't interfere with blood flow through the pulmonary veins or mitral valve. The distal portion of implant 250 comprises a plurality of anchors 256 (six are shown) that are adapted to expand within the LAA to secure themselves in the LAA. Anchors 256 are struts extending from tubular element 258. Blades 252 are also secured to tubular element 258.

FIGS. 16A-C illustrate an exemplary embodiment of an occlusion implant. FIG. 16A shows a perspective view, while FIGS. 16B and 16C show side and front views, respectively. Proximal portion 278 of implant 270 includes four larger blades 272 and two smaller blades 274 as shown in FIG. 15. Blades 272 and 274 are coupled to tubular hub 282, which has a lumen therethrough. The blades bend, or curve, slightly as they extend radially away from hub 282, which helps them better follow the contour of the atrial wall. Distal portion 280 of implant 270 includes a plurality of distal anchor 276 shown as wire forms extending from hub 282. While eight anchors 276 are shown, more or less anchors can be used. Anchors 276 each have two generally straight sections and a curved section in between. Anchors 276 extend slightly distally as they extend from hub 282.

FIGS. 17A-B illustrate an exemplary embodiment of an occlusion implant. Implant 290 includes relatively larger blades 292 and smaller blades 294 secured to hub 298. In the side view of FIG. 17B, it can be seen that the blades are axially staggered with respect to the adjacent blade. This can be accomplished by staggering the attachment points of the blades and hubs and the angle at which the blade extends from the hub can also be varied. Blades 292 and 294 are formed such that they extend from the hub initially in the distal direction, and then bend in the proximal direction, forming a curved configuration. The distal portion of implant 290, which is adapted to be anchored in the LAA, includes spokes, or struts 296, each with an anchoring end 299 adapted to either pierce the LAA tissue or improve the engagement with the LAA to better secure the implant in place.

FIG. 18 illustrates a side view of an exemplary embodiment of an occlusion implant. Implant 310 includes larger leaflets 312 and smaller leaflets 314, similar to other embodiments herein. Leaflets 312 are configured such that their radially outer portions extend further in the proximal direction than the radially outer portions of leaflets 314. The leaflets can be overlapped in an appropriate pattern to create a varying structural stiffness or to create a more dense blood barrier. There can be greater leaflet redundancy in the center region to cover the LAA ostium and prevent blood and/or clots to pass through. The configuration of leaflets 312 provides for better engagement with the atrial wall. The leaflets are secured to hub 316, which has a lumen therethrough. The distal anchor includes a plurality of spokes 318, each with an anchoring end as in the embodiment in FIGS. 17A and B.

Figure 19A:
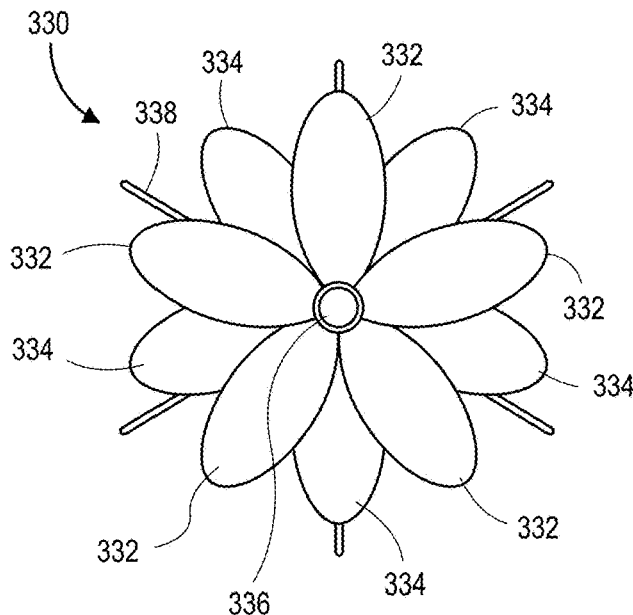
FIGS. 19A and 19B illustrate an exemplary embodiment of an implant.
Figure 19B:
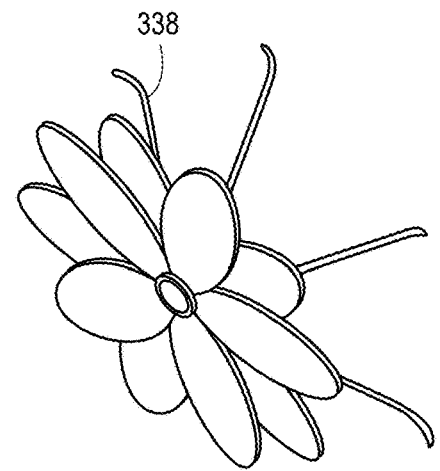

FIGS. 19A and 19B illustrate an exemplary embodiment of an implant. Implant 330 includes two rows of leaflets, similar to a flower petal design. The leaflets are attached to hub 336. A first set of leaflets 332 are aligned around hub 336, while leaflets 334 are aligned in a second row around hub 336. Leaflets 334 are disposed distally relative to leaflets 332. The distal portion of implant 330 includes spokes 338 to be anchored to the LAA tissue. FIG. 19B shows a perspective view of the embodiment in the front view of FIG. 19A. In an alternative embodiment, the leaflets are coupled to the hub around the periphery of the hub such that each leaflet is behind, or proximal to, the adjacent leaflet (except for one leaflet). This hub attachment pattern can ease in the collapse of the leaflets for delivery.

Figure 20A:
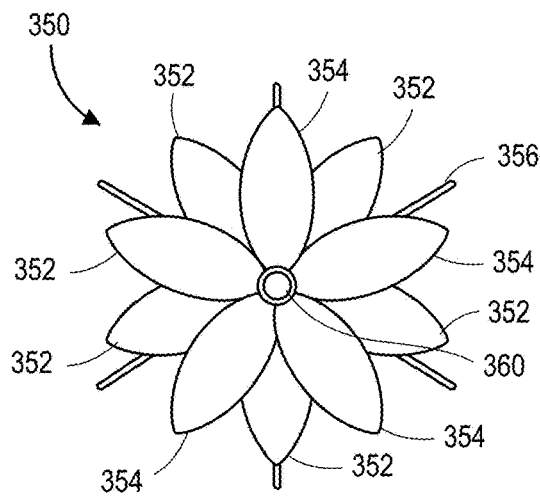
FIGS. 20A-20C illustrate another exemplary embodiment of an implant.
Figure 20B:
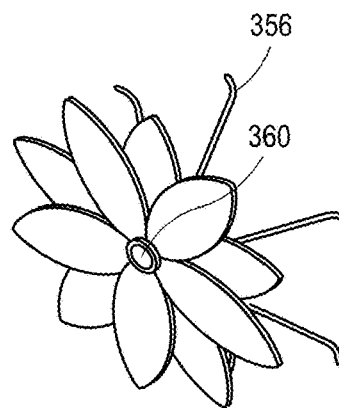
Figure 20C:
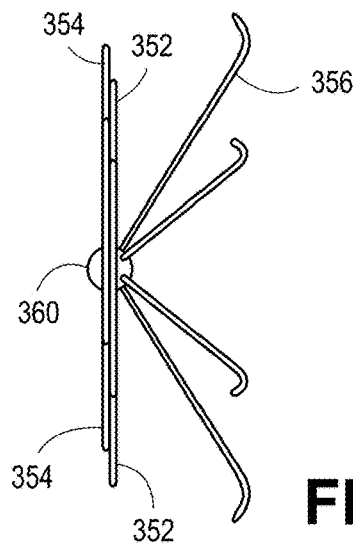

FIGS. 20A-C illustrate another exemplary embodiment. The leaflets are in two rows, as can be seen in the side view of FIG. 20C. The front, or proximal, row includes leaflets 354 (five are shown), while back, or distal, row includes leaflets 352 (five are shown). From the front view of FIG. 20A, it can be seen that each leaflet overlaps with the adjacent leaflet. This helps seal off the LAA and prevents blood flow into the LAA. The leaflets and distal anchors 356 are each coupled to hub 360, which has a spherical shape.

Figure 23:
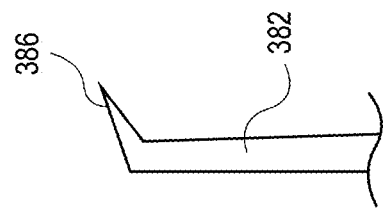
FIG. 23 illustrates an exemplary securing anchor.
Figure 22:
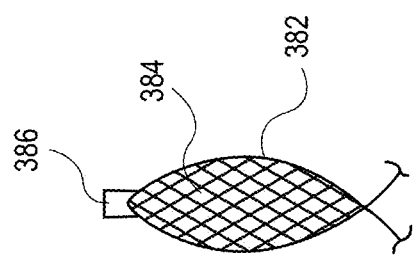
FIG. 22 illustrates an exemplary leaflet with barrier material attached thereto.
Figure 21:
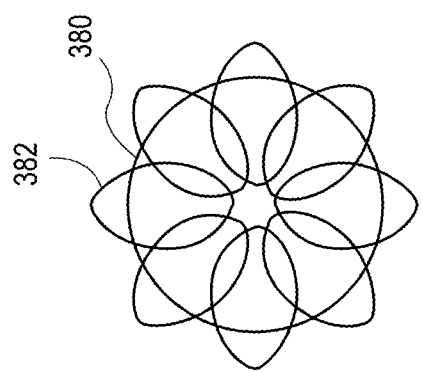
FIG. 21 illustrates the concept of an implant with a plurality of overlapping arms relative to the position of the left atrial appendage opening.

In any of the embodiments herein, the leaflet barrier material can be adapted to facilitate cell growth over and within the material. That is, after implantation, cells with grow over and within the barrier material, further isolating the LAA from the left atrium. In some of the embodiments, for example in FIGS. 14-20, there are small gaps between adjacent leaflets. This can be a way of adapting the device such that it acts like a filter rather than an occlusive barrier. The filter can allow blood to flow into the LAA from the left atrium, but will still prevent clots from exiting the LAA into the left atrium. FIG. 21 illustrates the concept of an implant with a plurality of overlapping arms 382 relative to the position of LAA opening 380. While the leaflets 382 cover most of the opening, small gaps can exist that allow blood to flow into the LAA, but are not large enough to allow clots to flow out. The small gaps therefore filter the clots and allow blood to flow through. FIG. 22 illustrates an exemplary leaflet 382 with barrier material 384 attached thereto. The leaflet also includes securing anchor 386 to help secure the leaflet to the atrial wall. FIG. 23 illustrates the securing anchor 386.

Figure 24A:
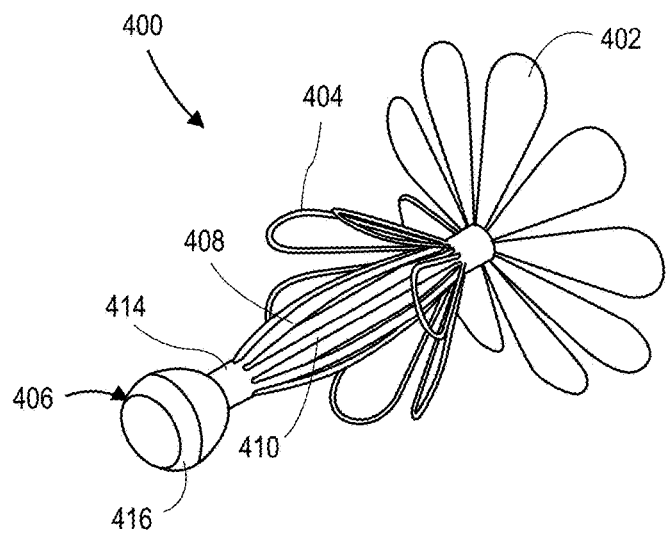
FIGS. 24A and 24B illustrate an exemplary embodiment of an implant that includes a secondary anchor adapted to be anchored in the distal region of the left atrial appendage.
Figure 24B:
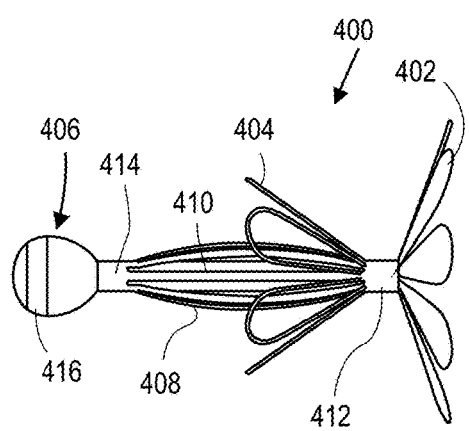

FIGS. 24A and 24B illustrate an exemplary embodiment of an implant that includes a secondary anchor adapted to be anchored in the distal region of the LAA. Implant 400 includes a proximal portion including leaflets 402 adapted to engage atrial tissue. Implant 400 also includes anchor elements 404 extending distally from hub 412. Leaflets 402 and anchoring elements 404 each have two generally straight portions connected by a curved portion. The anchoring element may be covered with a barrier, as previously sited, and may be pleated or ribbed to conform easily to various frame dimensions throughout the procedure. Adding a barrier to the anchor elements provides a redundancy, essentially two seal barriers to the LAA closure device. There are gaps between leaflets 402 allowing blood to flow therethrough but preventing clots from leaving the LAA. Implant 400 also includes a plurality of struts 408 extending from hub 412 to hub 414. Struts 408 can be formed by creating slots in a tubular element, leaving hubs 412 and 414 at the ends of the tubular element. The struts 408 can be biased in the configuration shown in FIGS. 24A-B. That is, that is their memory configuration that they can revert to if radially collapsed during delivery. This is similar to the concept shown in FIGS. 7A-7C. Hubs 412 and 414 define a lumen therein, through which elongate element 410 is disposed. Elongate element 410 has a lumen therein that can be accessed to deliver a variety of devices and/or substances into the LAA through elongate element 410. In FIGS. 24A and B, implant 400 also includes expandable bulb anchor 406, which is a material that is adapted to be inflated with an inflation fluid (liquid or gas). Upon inflation, it creates an interference fit with the LAA tissue, further assisting in the anchorage of the implant within the LAA. In some embodiments the bulb 406 is a Yulex-type material or other suitable material with a relatively large expansion ratio. In some embodiments the bulb has a memory configuration to which it is adapted to revert. The bulb would therefore expand and lock in place within the LAA.

In some embodiments the bulb includes cardiac monitoring and/or pacing capabilities described in more detail below. For example, the bulb can have sensing and/or stimulating electrodes incorporated therein or on the surface adapted to be in contact with LAA tissue. For example, bulb 406 can optionally include ring electrode 416 on the surface to be in contact with LAA tissue.

In an alternative embodiment to that shown in FIGS. 24A-B, the implant does not include a bulb, but rather a substance can be delivered into the LAA through elongate member 410, and out the distal end of hub 414. This concept is described in more detail herein.

Figure 25:
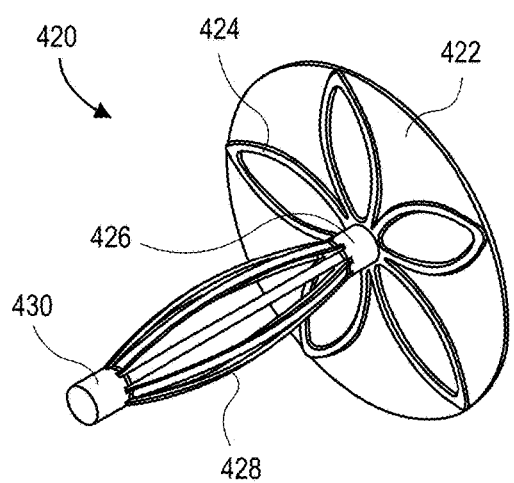
FIG. 25 illustrates an exemplary embodiment of an implant.
Figure 26:
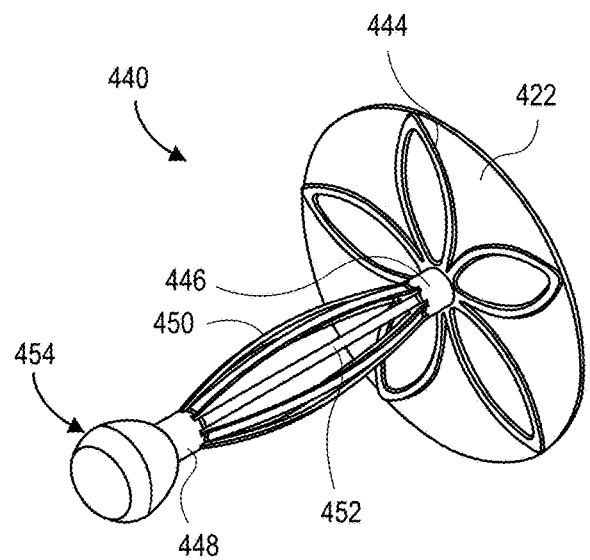
FIG. 26 illustrates implant with a barrier coupled to a frame.

FIG. 25 illustrates an exemplary embodiment. Implant 420 include barrier 422 adapted to prevent blood from entering the LAA (or at least preventing clots from leaving the LAA). Barrier 422 is reinforced by frame 424, which includes a plurality of reinforcing elements. Frame 424 is coupled to hub 426, from which struts 428 extend to hub 430. The struts and hubs can be formed as described herein or in any other suitable manner. FIG. 26 illustrates implant 440, with barrier 444 coupled to frame 442. Frame 442 is secured to hub 446, from which struts 450 extend to hub 448. Elongate element 452 and bulb 454 can be similar to their equivalents described in FIGS. 24A and 24B.

Figure 27:
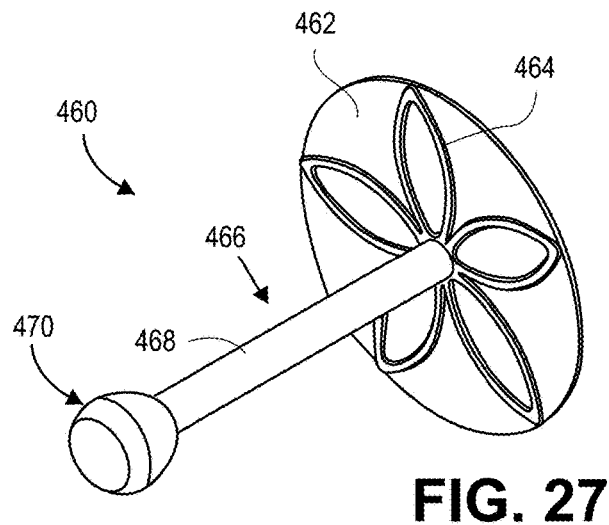
FIG. 27 illustrates implant which includes a barrier, a frame, a connector, and a bulb.

FIG. 27 illustrates implant 460, which includes barrier 462, frame 464, connector 466, and bulb 470. Connector 466 is a coil spring, which adds flexibility to the implant. Bulb is coupled to connector 466.

In some embodiments, once the anchors are secured around the LAA ostium and any other anchors are secured within the LAA, a procedure to verify the LAA is sealed from the left atrium can be performed. For example, in the embodiment shown in FIGS. 24A and 24B, once the bulb is expanded, dye can be injected through a lumen in the delivery device (e.g., a delivery catheter), through elongate element 410, and out a distal port in bulb 406. The LAA is sealed off from the atrium if, under fluoroscopy, it is determined that no injection contrast escapes the LAA.

In some embodiments, once a barrier is established between the left atrium and the LAA, a casting is injected through the distal port of the implant into the LAA. For example, the casting can be an electrically conductive casting or a soft polymer casting. In one particular example, ethylene vinyl alcohol ("EVOH") is injected with a conductive filler or a conductive polymer. The delivery catheter remains in place until the casting material has solidified and it cannot enter into the bloodstream.

As an alternative to a casting material, in some embodiments a sclerosant material is injected through the implant into the LAA. The sclerosant causes the LAA to shrink. The delivery catheter remains in place until the sclerosant is no longer active and cannot get into the blood stream.

FIG. 28 illustrates an alternative embodiment. Implant 480 includes ostium anchor 482 and LAA anchor 484. Anchor 482 includes barrier 488 that blocks the LAA from the atrium. Anchor 486 has a generally helical design. Anchor material 486 can be, for example without limitation, a wire, a ribbon material, and can be heat set to expand to an expanded configuration to anchor it within the LAA. In some embodiments anchor material 486 is a ribbon material coated with a hydrogel to enhance the tissue/anchor adherence. Optionally, a clotting agent is added to the hydrogel material. Optionally, cardiac diagnostic or monitoring components are located in anchor 482 to increase the electrical conduction between the monitoring component and the atrial wall.

FIG. 29 illustrates a further exemplary embodiment. The implant includes hydrogel capsule 502, secured in place within the LAA via struts or arms 504 and 508. The implant also includes diagnostic component 506. Arms 508 help anchor the implant in place and also connect diagnostic component 506 to atrial tissue. Diagnostic component 506 can monitor cardiac signals via arms 508, and can store date therein or can automatically transmit that date to an external device without storing it. The cardiac data can be accessed wirelessly using MEMS, or in some embodiments there can be direct access to diagnostic component 506 during a catheterization procedure. Capsule 505 can be filled with a hydrogel, or for example, a hydrogel/cyanoacrylate combination or other medical grade adhesives. Diagnostic component 506 can be adapted for long-term monitoring (e.g, weeks, months, or years). Subjects in which the implant can be implanted may suffer from atrial fibrillation. Diagnostic component 506 allows a physician to continuously monitor cardiac data to detect atrial fibrillation to prevent the patient from suffering a stroke. The diagnostic component can additional be adapted to communicate with an external device. The diagnostic component can continuously transmit patient information, such as cardiac electrical activity, to the external device. The external device could be worn by the patient or could be a physician's computer. The external device can, based on the patient data, detect atrial fibrillation. The external device can be adapted to transmit a signal to diagnostic component, with instructions to administer a therapy to the patient to attempt to disrupt the cardiac arrhythmia. In some embodiments the diagnostic component is adapted to detect the occurrence of atrial fibrillation and initial a therapy to disrupt the cardiac arrhythmia. Diagnostic component 506 can additionally be adapted to monitor other patient information, such as blood pressure, etc. Exemplary details of the cardiac monitoring and therapy are provided below.

FIG. 30 illustrate an exemplary embodiment in which implant 530 includes a plurality of expanding arms 532 coupled to hub 533. At the end of each of the arms is mechanical lock 534. Coiled wire 536 is coupled to hub 533 and extends in the proximal direction from hub 533. Arms 532 are adapted to expand and engage LAA tissue to lock the implant in the LAA. Coiled element 536 is adapted to engage tissue surrounding the LAA ostium and is adapted to monitor cardiac electrical activity and optionally pace the tissue to disrupt atrial fibrillation and prevent stroke. In some embodiments the implant relies on MEMS for the diagnostic components and optional wireless communication. Implant 530 can be adapted to incorporate any features disclosed herein, such as being adapted to deliver a casting material into the LAA to form a plug filling the LAA space.

Figure 31A:
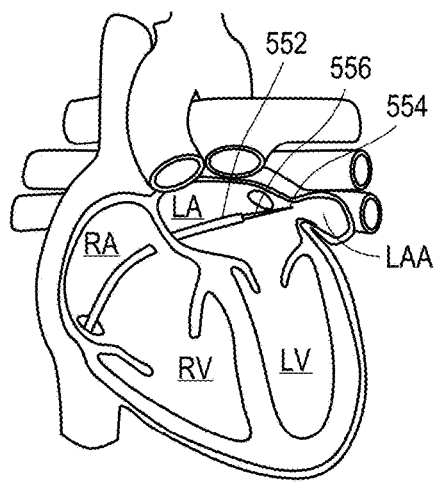
FIGS. 31A-F illustrate an exemplary method of access to the left atrial appendage and an exemplary implant to be implanted within a patient.
Figure 31B:
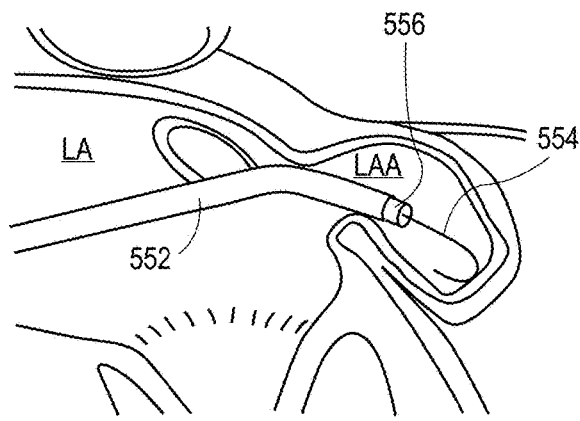
Figure 31C:
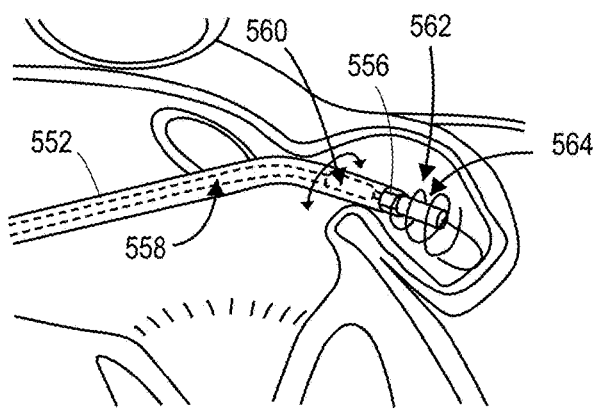
Figure 31D:
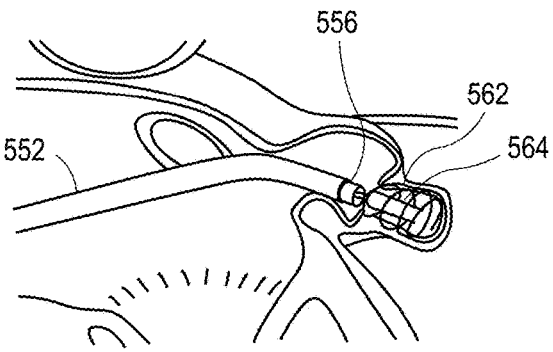
Figure 31E:
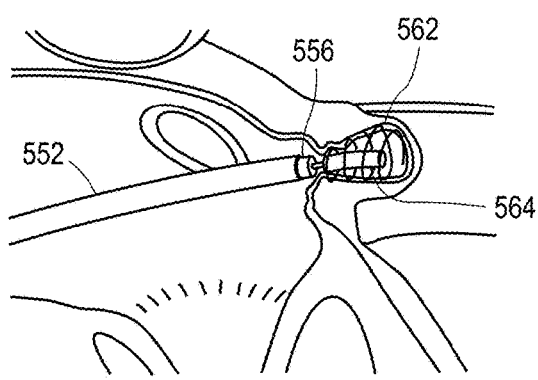
Figure 31F:
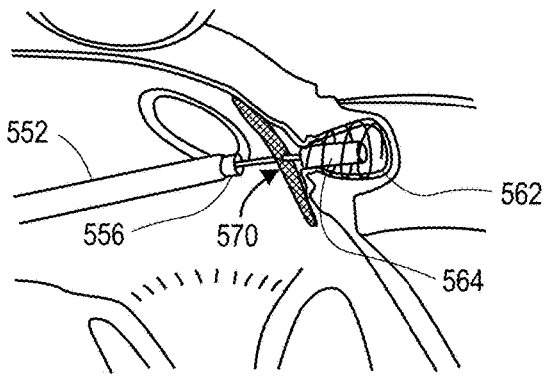

FIGS. 31A-F illustrates an exemplary method of access to the LAA and an exemplary implant to be implanted within a subject. In FIG. 31A, delivery sheath 552, implant sheath 556, and guidewire 554 gained access to the LAA via a femoral vein, inferior vena cava, right atrium, fossa ovalis, and left atrium approach, an approach known in the art. The LAA can be accessed via other routes as well. Additionally, the implant can be positioned surgically. Other minimally invasive approaches can be used. In FIG. 31B, guidewire 554 is extended into the LAA as shown. Steerable delivery sheath 552 and implant sheath 556 are tracked over guidewire 554 into the LAA into the position shown in FIG. 31B. Once the distal end of the steerable sheath 552 is within the LAA, implant sheath 556 is then exposed. As shown in FIG. 31C, corkscrew drive 558 is rotated causing the corkscrew portion 562 of the implant to be deployed from the distal end of the implant sheath 556. The corkscrew has a tapered configuration. As the corkscrew is advanced, plug 564 is exposed and the rotation of corkscrew 562 penetrates the LAA tissue, while applying very little tensile or compressive forces on the LAA. Plug 564 is made of a spongetype material adapted to expand in diameter in the presence of blood. FIG. 31D shows the corkscrew 562 fully deployed/rotated and the LAA tissue tapered down the corkscrew until it is "pinched" between the corkscrew and the ID plug. In FIG. 31E, once the LAA tissue is securely grasped by the implant, the entire system is retracted proximally. This actuation causes the LAA to collapse and compress. The corkscrew and plug provide a grasping mechanism which supports the weak LAA tissue to prevent tearing during collapse and compression. The final step in the method is to deploy anchoring barrier 570 in the left atrium against the atrial wall, as shown in FIG. 31F. Note that the sequence of deployment is easily altered to deploy 570 first, therefore sealing the entrance to the LAA from the atrial pressure and then affixing the corkscrew to the distal area of the LAA. This would potentially address safety concerns of the corkscrew causing the LAA to leak. The barrier maintains a constant tension on the collapsed/compressed LAA. The barrier, as shown, is a braided nitinol material with a liner made from, for example, ePTFE. Other barrier material and designs can be used. The liner blocks blood flow into the LAA. The corkscrew drive is the released from the proximal portion of the implant, leaving the implant within the patient.

Figure 33:
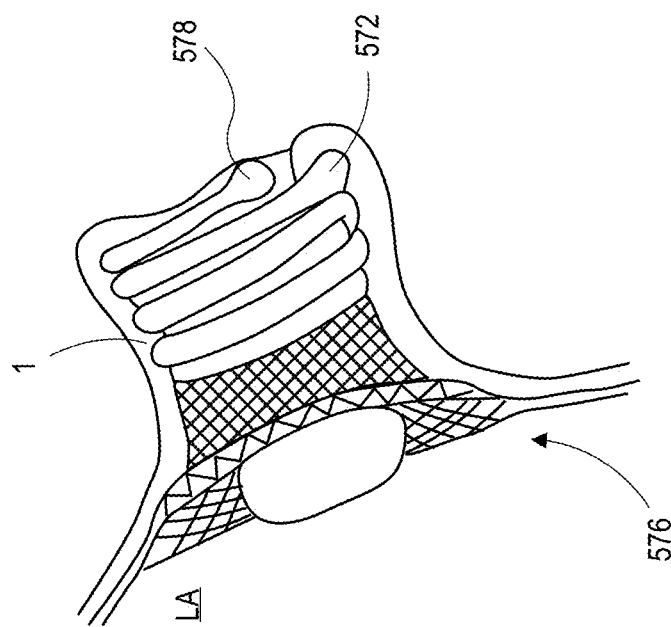
FIG. 33 illustrates the implant from FIG. 32 in a left atrial appendage.
Figure 32:
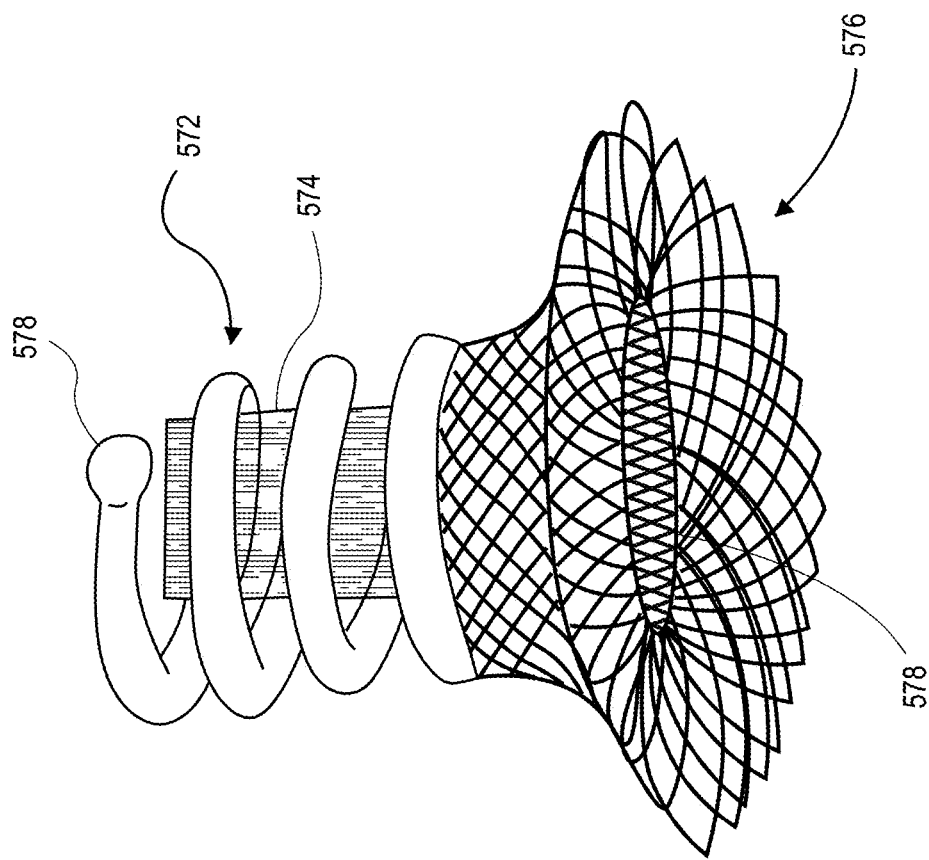
FIG. 32 illustrates an exemplary embodiment in which the implant includes non-tapering corkscrew.

FIG. 32 illustrates an exemplary embodiment in which the implant includes corkscrew 572 that is not tapered as in the embodiment in FIG. 31. At the distal end of corkscrew is bulb 578 that can prevent damage to LAA tissue. The implant also includes plug 574 and proximal anchoring portion 576, comprising a braided material, such as nitinol, and barrier 578 adapted to block blood flow into the LAA. FIG. 33 illustrates the implant from FIG. 32 in a LAA.

The systems herein can also include a cardiac monitoring component to monitor one or more patient parameters. In some embodiments the systems include a monitoring component adapted to monitor electrical activity of the heart over time. The electrical activity of the heart can be monitored to detect arrhythmias, such as atrial fibrillation. In some embodiments the systems herein are adapted to provide a therapy to treat the detected arrhythmia. For example, if an arrhythmia is detected, the system can be adapted to pace cardiac tissue through electrical stimulation thereof. Alternatively, or in addition to, the systems can be adapted to deliver a therapeutic compound to the patient in the event an arrhythmia is detected. The monitoring and/or therapy components of the systems can optionally be a stand-alone device and not integrated into a LAA occlusion device.

In some embodiments the system includes a monitoring component that monitors, or senses, cardiac electrical activity. The sensing components can be positioned within the LAA and/or the left atrium, and are adapted to be in contact with cardiac tissue to sense the electrical activity. The system can monitor ECG data from the patient. In some embodiments the sensing component is an electrode or an array of electrodes in contact with cardiac tissue to monitor electrical activity of the heart.

The system is adapted to process the electrical activity data and detect atrial fibrillation from the monitored data. For example, the system can monitor ECG data and detect AF by, for example, the absence of P waves, with unorganized electrical activity in their place. Irregular R-R intervals due to irregular conduction of impulses to the ventricles can also be an indication of atrial fibrillation. The system can include software adapted to automatically detect the occurrence of AF. The system can also be adapted such that electrical activity data is transmitted to health care professionals whose interpretation of the electrical activity data can supplement or replace the automated detection process.

The detection component can be integrated with the monitoring components such that it is within the heart. Alternatively the processing component can be disposed outside the heart, and optionally external to the patient. If outside the heart, the processing component can be secured to, for example, the epicardium, or it could be a device that is worn by the patient close to the heart and that is in wireless communication with the intra-cardiac device.

In some embodiments the processing components are disposed within the heart and part of the monitoring device. The intra-cardiac system can then monitor and detect atrial fibrillation from a device implanted completely within the LAA and/or the left atrium.

In some embodiments the processing components of the system are disposed in a device external to the heart such that monitored patient data is transmitted, wirelessly or wired, to the processing component. If AF is detected therapy will likely be administered as soon as possible, and thus the monitoring component substantially continuously transmits data to the processing component such that substantially real-time detection of AF occurs.

If AF is detected, the system can be adapted to administer therapy to restore normal electrical activity to the heart. In some embodiments the therapy is electrical pacing therapy administered by, for example, pacing electrodes disposed within the LAA and/or left atrium. Electrical impulses can be delivered by electrodes that contact the cardiac muscle to pace the appendage or atrium for a short-term period of time to treat, for example, AF, atrial tachycardia, sick sinus rhythm, etc. In some embodiments pacing occurs at regular intervals. For example, pacing can occur for about 30 to about 90 seconds and occurs about every 6 to about every 12 hours. These numerical ranges are merely exemplary.

In some embodiments the therapy comprises delivering a therapeutic agent into the heart upon the detection of an arrhythmia. The implantable system can include a drug reservoir for delivery of one or more anti-atrial fibrillation drugs if the patient goes into AF. In some embodiments the LAA occlusion device is placed near the ostium of the LAA, while the cardiac monitor and drug reservoir are disposed on the appendage side of the implant. The cardiac monitor is adapted to release a prescribed amount of the therapeutic agent in the event AF is detected and lasts longer than a prescribed period of time. The therapeutic agent administered includes anti-arrhythmic and/or rate control and/or anticoagulation agents for AF. An example is Vernakalant, an investigational drug under regulatory review for the acute conversion of AF. Exemplary rate control agents and doses include Metoprolol (e.g., about 50 to about 100 mg), Atenolol (e.g., about 50 to about 100 mg), Propranolol (e.g., about 40 to about 80 mg), Acebutolol (e.g., about 200 mg), Carvedilol (e.g., about 6.25 mg), Diltiazem (e.g., about 180 to about 240 mg), Verapamil (e.g., about 180 to about 240 mg), and Digoxin (e.g., about 0.125 mg). Exemplary rhythm control agents and doses include Propafenone (e.g., about 450 mg), Flecainide (e.g., about 200 mg), Sotalol (e.g., about 240 mg), Dofetilide (e.g., about 500 mcg), Amiodarone (e.g., about 200 mg), Quinidine (e.g., about 600 to about 900 mg). In some embodiments innovative anti-arrhythmic agents can be used with unconventional anti-arrhythmic mechanisms, such as stretch receptor antagonism, sodium-calcium exchanger blockade, late sodium channel inhibition, and gap junction modulation. These therapies have not yet reached clinical studies in AF but reports look promising.

In FIG. 1, anchoring element 16 can incorporate sensing elements such as ring electrodes disposed on and around anchoring element 16. Anchoring element 16 can also incorporate pacing, or stimulating, electrodes disposed thereon. Any suitable anchoring element or anchoring structure described herein can be adapted to include one or more electrodes for monitoring and/or pacing. For example, in FIG. 3, anchor 44 can be adapted to have one or more electrodes disposed thereon. The electrodes would be adapted to be in contact with LAA tissue to monitor and/or pace the tissue. Similarly, distal anchor 56 can also comprise electrodes disposed thereon to monitor and/or pace LAA tissue.

In some embodiments, even if there is an anchoring structure within the LAA, an anchoring structure adjacent the LAA ostium can have electrodes disposed thereon to monitor and/or pace tissue adjacent the ostium. For example, in the embodiment in FIG. 3, anchoring structure 46 can include electrodes disposed thereon. In FIG. 12, distal anchor can include monitoring and/or pacing electrodes thereon. In some embodiments, connector 146 can be used as either the anode or the cathode and an electrode within distal anchor 148 is the opposite of the electrode in connector 146. Connector 146 is electrically coupled to the electrode in distal anchor 148.

FIGS. 14A-27 illustrate exemplary embodiments of how occluding devices described herein can be adapted to include monitoring and therapy components. For example, leaflets 202 in the embodiment in FIGS. 14A-C can be adapted to include sensing and/or pacing electrodes. When the leaflets are expanded in the left atrium, the distal sides of the leaflets engage atrial tissue. The leaflets, and optionally frame 101, can have electrodes disposed therein and can be in electrical connection to hub 212 to other components that can provide power. Additionally, in the embodiment in FIGS. 16A-16, hub 282 has a lumen therein that can be adapted to receive an elongate member that is to be disposed within the LAA. The elongate member can have one or more monitoring and/or pacing electrodes thereon to be in contact with LAA tissue. In FIGS. 24A and 24B, elongate element 410 can be the cathode or anode while electrode 416 of bulb 406 is the opposite thereof. Electrode 416 is adapted to be in contact with LAA tissue and is adapted to monitor and/or pace the cardiac tissue.

While the implanted devices can be incorporated with sensing and/or stimulating functionality, the implanted devices, in some embodiments, include circuitry to process the monitored patient data and detect an arrhythmia. Processing the data can include known techniques, including filtering and amplifying a signal. Algorithms stored in the device can determine if, based on the data, AF is occurring. Upon the detection of an arrhythmia, the system can be adapted to automatically deliver a therapy, whether it is electrical pacing, drug delivery, or some other type of therapy.

In some embodiments the processing and detecting steps occur in a device external to the heart, whether they are underneath the patient's skin or external to the patient. For example, an external device can be secured to the patient using a harness such that the device is secured comfortably near the patient heart. The monitored data is transmitted to the external device, which can include the processing and detection components. Once an arrhythmia is detected, the external device then communicates a signal to the internal device to initiate the therapy. In some instances the data, raw or processed, is further transmitted to a remote location. For example, the data can be transmitted to a physician for review. In some instances the detection algorithm can be reprogrammed as needed, perhaps to provide better more accurate AF detection.

The implanted device or any external device can include memory to store data, either temporarily or permanently. The implanted device can store a certain amount of data, such as in a first-in-first-out process, or it can transmit data to an external data, which then stores the data. In some embodiments only data just before, during, and following AF is desired. The system can be adapted to store in memory only data from that specific period of time. The stored data can additionally be reviewed by a health care provider as desired.

The implantable device can optionally include a power source, which is optionally rechargeable (such as by inductive charging). The power source can power the sensing and/or pacing electrodes, or any other electrically driven activities performed by the implant. The power source is disposed in the implant and is in electrical communication with any monitoring and/or pacing electrodes.

The device can be adapted with additional sensors to acquire data to calculate or determine any of the following: AF burden (i.e., the time the patient is in AF as compared to sinus rhythm), left atrial pressure, temperature, transthoracic impedance (surrogate for pulmonary fluid status, i.e., "CHF"), impending atrial fibrillation or ventricular fibrillation. The implant can also include a pulse counter.

Figure 34B:
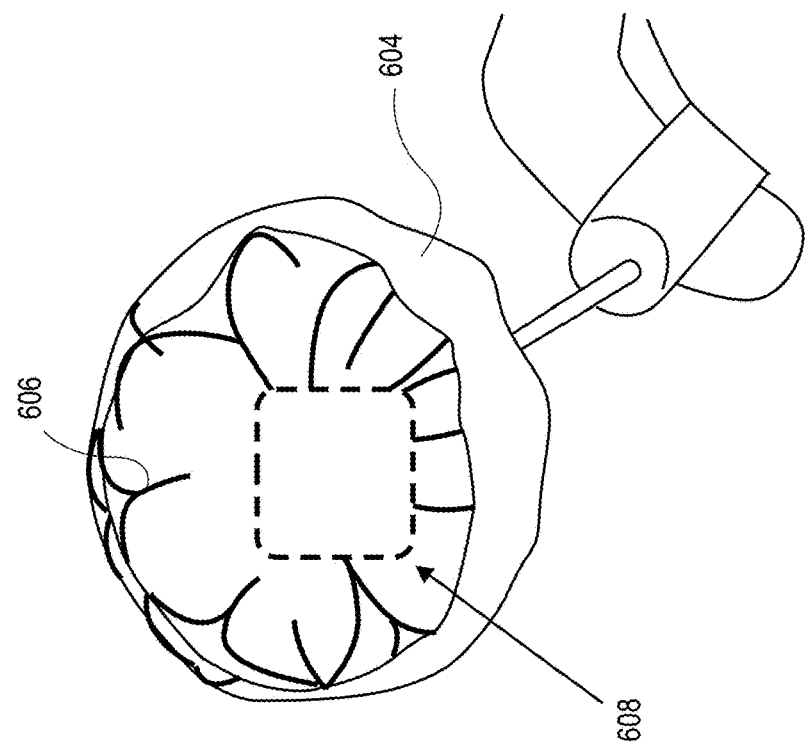
FIGS. 34A and 34B illustrate an alternative embodiment in which implant is adapted to occlude flow into the left atrial appendage, monitor patient data, and dispense a therapeutic agent into the left atrial appendage if an arrhythmia is detected.
Figure 34A:
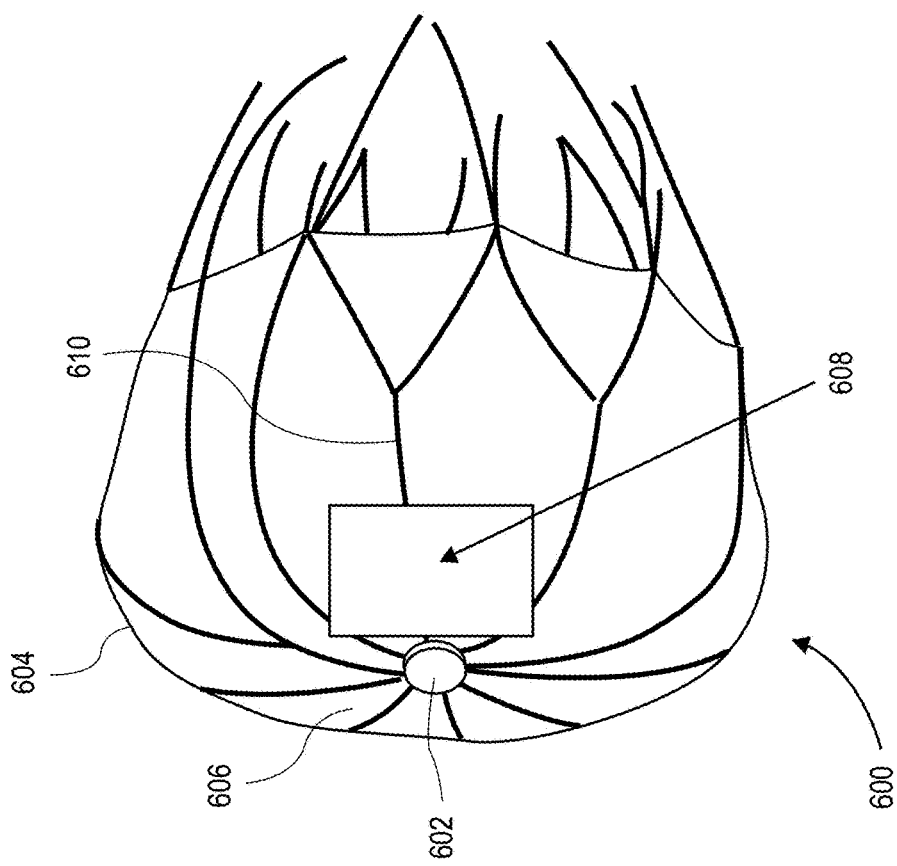

FIGS. 34A and 34B illustrate an alternative embodiment in which implant 600 is adapted to occlude flow into the LAA, monitor patient data, and dispense a therapeutic agent into the LAA if an arrhythmia is detected. Implant 600 include expandable frame 606, which has a general mushroom configuration in an expanded configuration. The frame is secured to barrier 604, which is adapted to prevent blood from entering the LAA. Barrier 604 only covers a proximal portion of frame 604, leaving a distal portion of frame 606 uncovered by the barrier. The open end of the frame faces into the LAA. The implant also includes delivery element 602 that is adapted to be releasably coupled to a delivery tool (not shown). Implant 600 also includes cardiac monitor and therapeutic agent reservoir component 608. Component 608 is secured to the inside of the implant 600. That is, component 608 is only exposed to the inside of the LAA and not the left atrium. The cardiac monitoring component is electrically coupled to LAA tissue via leads 610 and monitors atrial activity, such as electrograms. When the detection component (whether it is integrated with implant 600 or disposed external to the heart) detects an arrhythmia such as atrial fibrillation, component 608 can be programmed to automatically release a dose of an anti-atrial fibrillation therapeutic agent. The drug reservoir could be a reservoir with a valve that when opened, releases the agent into the LAA. The valve, or any suitable actuatable element, can be electrically powered by the power source within implant 600 to open to release the agent into the LAA.

Figure 35:
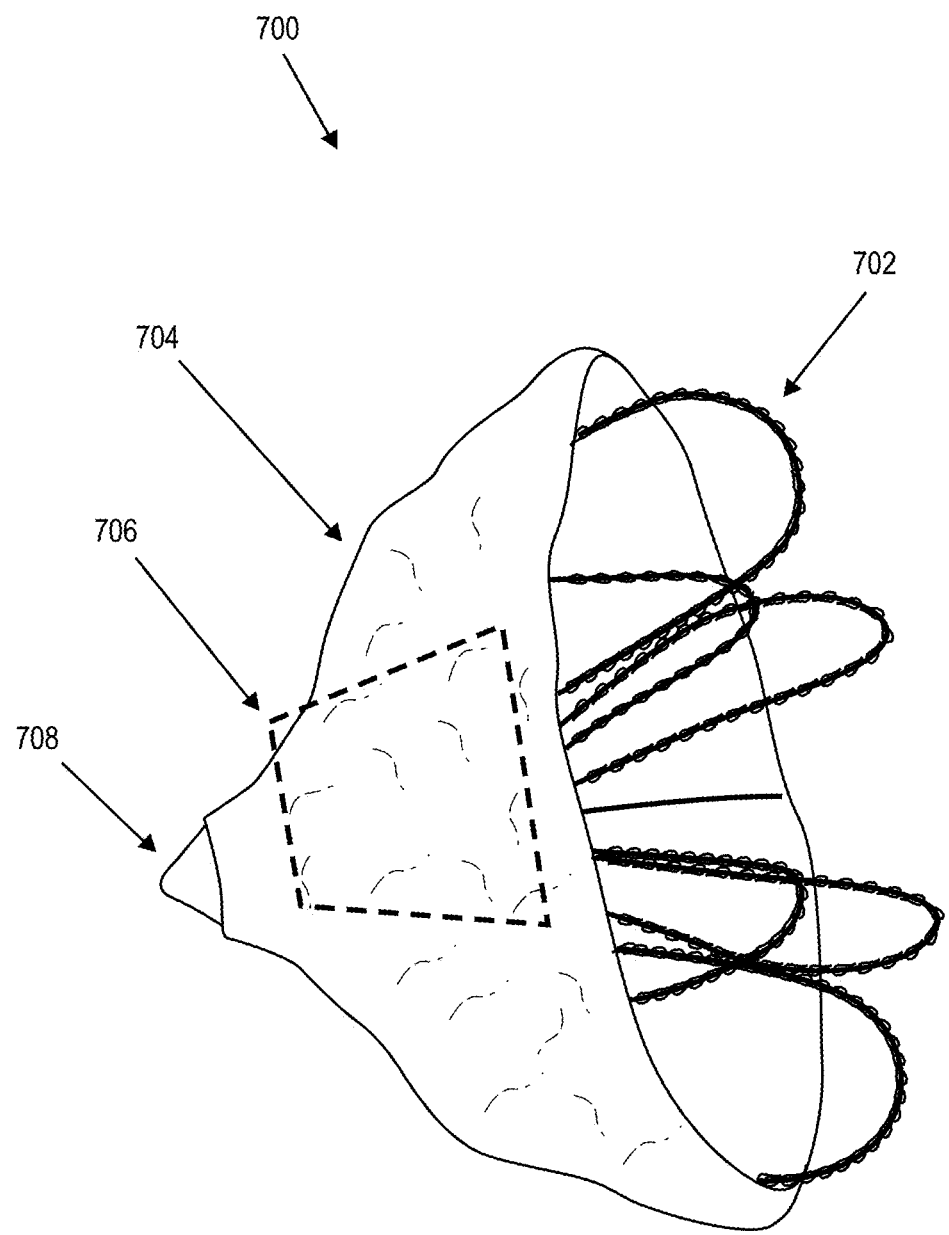
FIG. 35 illustrates an alternative embodiment of an implant similar to the implant shown in FIGS. 34A and 34B.

FIG. 35 illustrates an alternative embodiment of implant 700 that is similar to implant 600 shown in FIGS. 34A and 34B. Implant 700 includes expandable frame 702, barrier 704, which is adapted to prevent blood from entering the LAA. Barrier 704 only covers a proximal portion of frame 702, leaving a distal portion of frame uncovered by the barrier. The open end of the frame faces into the LAA. The implant also includes delivery element 708 that is adapted to be releasably coupled to a delivery tool (not shown). Implant 700 also includes cardiac monitor and therapeutic agent reservoir component 706, which can provide the same functions as component 608 in the embodiment in FIGS. 34A and 34B.

Figure 37A:
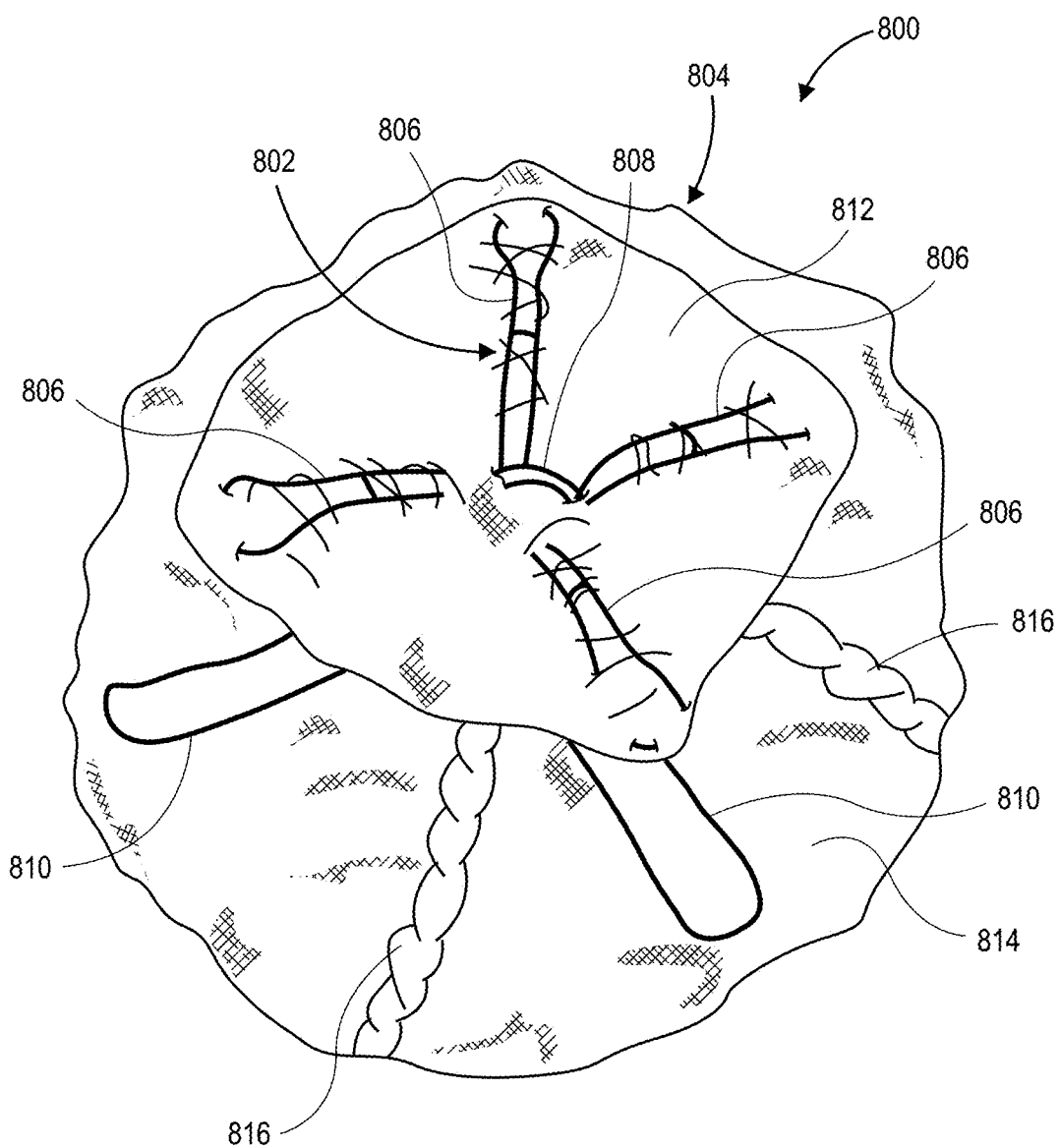
FIGS. 37A-C illustrate an exemplary embodiment of a medical device in an expanded, or deployed, configuration that is adapted to isolate material in the left atrial appendage.
Figure 37B:
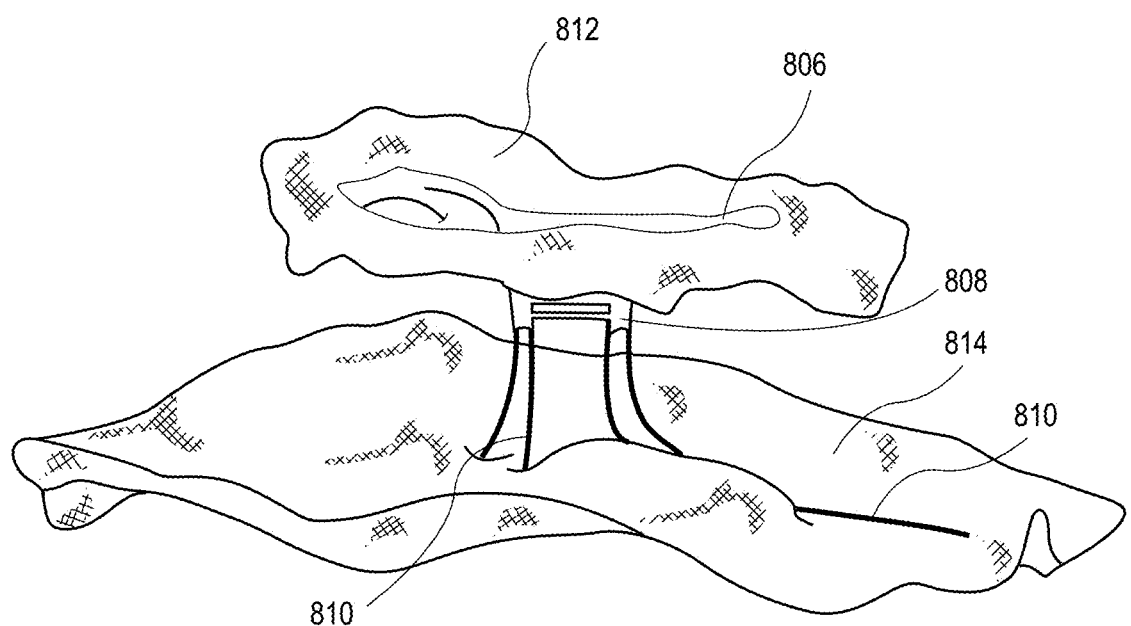
Figure 37C:
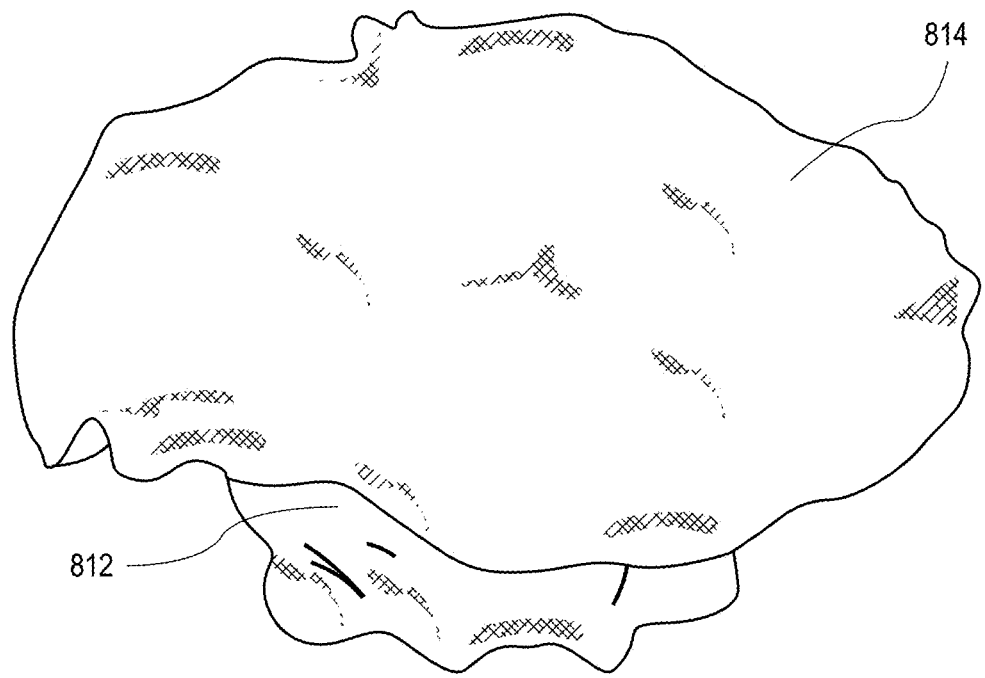

FIGS. 37A-C illustrate an exemplary embodiment of a medical device in an expanded, or deployed, configuration that is adapted to isolate material in the left atrial appendage. Device 800 includes anchoring portion 802 and barrier portion 804. Anchoring portion 802 includes four distal anchors 806 and four proximal anchors 810 (only two can be seen), all of which are coupled to hub 808. Barrier portion 804 includes proximal barrier 814 and distal barrier 812. Distal barrier 812 is secured to distal anchors 806, while proximal barrier 814 is secured to distal anchors 810. In this embodiment they are secured with sutures, as shown.

Each of the distal and proximal anchors has a looped configuration, the two ends of which are secured to hub. The loops are longer than they are wide. In their expanded configurations, the anchors 806 and 810 extend substantially radially outward from hub 808, and are generally orthogonal to the longitudinal axis of hub 808. In other words, in the side view shown in FIG. 37B, the anchoring portion resembles the letter "H," with the distal anchors 806 shorter than proximal anchors 810. All of the distal anchors 806 are generally in the same plane, but are constructed to be appropriately flexible to conform to the amorphous anatomy of the left atrial appendage, which is generally orthogonal to the longitudinal axis of hub 808, which can be seen in the side view of FIG. 37B. All of the proximal anchors are also generally in a single plane, which is generally orthogonal to the longitudinal axis of hub 808.

In this embodiment the anchoring portion, including the eight anchors and the hub, is formed by laser cutting a single nitinol tube. The anchors and hub need not be formed from the same starting material, and can be secured to one another, such as by welding. The hub and the anchors need not be the same type of material. Materials other than nitinol can be used, and other cutting methods can be used.

In this embodiment, after the necessary material has been removed during the laser cutting process, the eight anchors are heat set in the deployed configurations shown in FIGS. 37A-C, such that they are substantially orthogonal to hub 808. Barrier 814 and barrier 812 are then secured to the anchors. In this embodiment they are sutured to the anchors, with the sutures as shown. Other methods of securing the anchors and barriers can be used. The proximal anchors 810 are secured to proximal barrier 814 such that proximal anchors 810 are on the distal side of proximal barrier 814. Distal anchors 806 are secured to distal barrier 812 such that distal anchors 806 are disposed on the distal side of distal barrier 812. For distal anchors 806 to be on the distal side of distal barrier 812, there is a central hole in distal barrier 812.

The barriers can be a polyester material such as polyethylene terephthalate ("PET"; trade name Dacron®). The barriers can be other suitable materials, such as PTFE.

Proximal barrier 814 has pleats 816 formed therein between anchors 810. The pleats, or other rib formations, can help reduce the amount of material in the barrier, which can make it easier when the device is loaded into a delivery device. The pleats can help reduce the delivery profile of the device. The pleats or ribs also make it easier to accommodate dimensional changes of the anchor elements with compression on the barrier in the delivery configuration and tension on the barrier in the deployed configuration. Maintaining a low barrier thickness can also ease the loading process and maintain a minimal delivery profile of the device. The barrier material can be selected to have a specific porosity. The device includes two barriers 814 and 812, which effectively creates a two-ply barrier, and thereby reduces the amount of material that can escape the left atrial appendage and into the left atrium.

The barriers are adapted to prevent blood flow into the LAA, although they could be adapted to filter blood such that they prevent clots from flowing from the LAA into the left atrium. In alternative embodiments the device does not include distal barrier 812, such that the device only includes a proximal barrier.

In an exemplary method of use, the device is used to occlude the left atrial appendage such that material in the left atrial appendage cannot enter the left atrium. Device 800 is first loaded into a delivery configuration in a delivery device, such as a catheter. Distal anchors 806 are deformed by collapsing them toward the longitudinal axis of the hub, so that they extend generally distally from the hub and are moved closer to one another. Proximal anchors 810 are also collapsed towards the longitudinal axis of the hub, moving them closer together such that they extend substantially proximally from the hub. The reconfiguration of proximal anchors 810 causes the barrier material 814 to bunch up, which is minimized by pleats, ribs, or other similar features. Pleats or ribs can also be incorporated into the distal barrier 812. The device can be front-loaded into a distal end of the delivery device, such that the proximal anchors are deformed before the distal anchors.

In use, after the device has been advanced within the patient adjacent the left atrial appendage (as described above), the distal anchors and distal barrier are first deployed from the delivery device into the left atrial appendage. Anchors 806 deform towards their deployed configuration shown in FIGS. 37A-C, such that they extend radially from hub 808. As they deform, they will engage left atrial appendage tissue, anchoring the distal portion of the device in the left atrial appendage. Once the position of the anchors in confirmed using one or more imaging techniques, the proximal anchors are then deployed from the delivery device such that the proximal anchors engage left atrial tissue and secure the proximal barrier over the left atrial appendage ostium. Material in the left atrial appendage cannot escape the appendage and enter the atrium. The proximal anchors can have a deployed configuration in which they extend slightly distally relative to the hub, such that they apply a slight distally directed force on the atrial tissue, which helps anchor device in place relative to the atrial tissue. Similarly, the distal anchors can be biased to extend slightly in the proximal direction relative to the hub to apply a slightly proximally directed force on the left atrial appendage. In some embodiments the distal anchors and proximal anchors provide a slight or substantially clamping effect on the tissue at the ostium, which helps secure the device in place.

It should be noted that before the proximal anchors are deployed, if the position of the deployed distal anchors is not optimal, the catheter can be advanced distally, deforming the distal anchors forward towards their delivery configurations, while recapturing the distal anchors within the delivery device.

Device 800 can similarly be adapted to include sensing and/or treatment features to sense and treat cardiac arrhythmias. For example, one or more of the anchors 810 or 806 can have one or more electrodes disposed thereon adapted to delivery energy to cardiac tissue to pace the tissue in the event of a detected atrial fibrillation. Alternatively, hub 808 can have a cylindrically shaped drug delivery device disposed therein, which is adapted to deliver a drug or other agent into the left atrial appendage, examples of which are disclosed above.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A left atrial appendage (LAA) occlusion implant, comprising:
    a proximal portion comprising multiple sized leaflets adapted to engage the atrial wall around the LAA, the multiple sized leaflets include:
        a first set of leaflets sized to not obstruct blood flow through the mitral valve or the pulmonary vein; and
        a second set of leaflets, larger than the first set of leaflets, sized to provide more surface contact with the atrial wall than the first set of leaflets,
    the multiple sized leaflets having:
        a frame element having a triangular or elliptical shape made from shape memory material with two ends coupled to a hub;
        a barrier covering the frame element, the barrier being adapted to prevent blood clots from passing through the LAA;
        wherein the frame element includes an outer portion adapted to collapse into a delivery configuration and self-expand when delivered; and
    a distal portion comprising a plurality of anchors having a triangular or elliptical shape made of a shape memory material with two ends coupled to the hub, the plurality of anchors having an outer portion adapted to collapse into a delivery configuration and self-expand when delivered.

2. The implant of claim 1, wherein a central portion of each frame element is adapted to bend outward to ease in the collapse of the frame element, and a central portion of each anchor is adapted to bend outward to ease in the collapse of the anchors.

3. The implant of claim 1, wherein the multiple sized leaflets are adapted to overlap one another into a staggered orientation when collapsed.

4. The implant of claim 1, wherein the multiple sized leaflets and anchors are adapted to be delivered through a delivery instrument.

5. A left atrial appendage (LAA) occlusion implant, comprising:
    a proximal portion comprising multiple sized leaflets adapted to engage the atrial wall around the LAA, the multiple sized leaflets include:
        a first set of leaflets sized to not obstruct blood flow through the mitral valve or the pulmonary vein; and
        a second set of leaflets, larger than the first set of leaflets, sized to provide more surface contact with the atrial wall than the first set of leaflets;
    the multiple sized leaflets having:
        a frame element having a triangular or elliptical shape with two ends coupled to a tubular element;
        a barrier covering the frame element, the barrier being adapted to prevent blood clots from passing through the LAA; and
    a distal portion comprising a plurality of struts extending from the tubular element and adapted to expand within the LAA to secure the implant.

6. The implant of claim 5, wherein the frame element is made of a shape memory material adapted to collapse into a delivery configuration and self-expand when delivered.

7. The implant of claim 5, wherein the struts are made of a shape memory material and adapted to collapse into a delivery configuration and self-expand when delivered.

8. A left atrial appendage (LAA) occlusion implant, comprising:
    a proximal portion comprising multiple sized leaflets adapted to engage the atrial wall around the LAA, the multiple sized leaflets include:
        a first set of leaflets sized to not obstruct blood flow through the mitral valve or the pulmonary vein; and
        a second set of leaflets, larger than the first set of leaflets, sized to provide more surface contact with the atrial wall than the first set of leaflets,
    the multiple sized leaflets having:
        a frame element having a triangular or elliptical shape with two ends coupled to a tubular hub;
        a barrier covering the frame element, the barrier being adapted to prevent blood clots from passing through the LAA; and
    a distal portion comprising a plurality of anchors with two generally straight sections extending from the tubular hub with a curved section in between.

9. The implant of claim 8, wherein the frame element is made of a shape memory material adapted to collapse into a delivery configuration and self-expand when delivered in the LAA.

10. The implant of claim 8, wherein the anchors are made of a shape memory material and adapted to collapse into a delivery configuration and self-expand when delivered.

11. A left atrial appendage (LAA) occlusion implant, comprising:
    a proximal portion comprising:
        a first set of leaflets sized to not obstruct the blood flow through the mitral valve or the pulmonary vein and made from shape memory material coupled to a hub in a first row; and
        a second set of leaflets, larger than the first set of leaflets, sized to provide more surface contact with the atrial wall than the first set of leaflets and made from shape memory material coupled to a hub in a second row, the second set of leaflets disposed distally relative to first set of leaflets;
        the second set of leaflets configured to overlap the first set of leaflets creating a barrier configured to engage the atrial wall around the LAA and seal off the LAA to prevent blood flow into the LAA; and
    a distal portion comprising a plurality of anchors made of a shape memory material with a first end coupled to the hub and a second end configured to engage the LAA to secure the implant;
    wherein the first set of leaflets, second set of leaflets, and plurality of anchors are configured to collapse into a delivery configuration such that they can be delivered endoluminally to the LAA in a delivery sheath or catheter, then self-expand once delivered to the LAA.

12. The implant of claim 11, wherein the first and second leaflets include:
    a frame having a triangular or elliptical shape with two ends coupled to the hub; and
    a barrier covering the frame element, the barrier being adapted to prevent blood clots from passing through.

13. The implant of claim 11, wherein the first set of leaflets are small leaflets and the second set of leaflets are large leaflets, the large leaflets having outer portions configured to extend further in the proximal direction than outer portions of the small leaflets.

14. The implant of claim 11, wherein the first and second set of leaflets are adapted to overlap one another in a staggered orientation when collapsed into the delivery configuration.

15. The implant of claim 11, wherein the first set of leaflets and the second set of leaflets are adapted to collapse downward in the proximal direction to be disposed within a delivery catheter, sheath, or other delivery instrument, and the plurality of anchors are adapted to collapse downward in the distal direction to be disposed within the delivery catheter, sheath, or other delivery instrument.

* * * * *